US009969829B2

(12) United States Patent
Domon et al.

(10) Patent No.: US 9,969,829 B2
(45) **Date of Patent: *May 15, 2018**

(54) POLYMER COMPOUND, NEGATIVE RESIST COMPOSITION, LAMINATE, PATTERNING PROCESS, AND COMPOUND

(71) Applicant: SHIN-ETSU CHEMICAL CO., LTD., Tokyo (JP)

(72) Inventors: Daisuke Domon, Jyoetsu (JP); Koji Hasegawa, Jyoetsu (JP); Keiichi Masunaga, Jyoetsu (JP); Masaaki Kotake, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/399,220

(22) Filed: Jan. 5, 2017

(65) Prior Publication Data

US 2017/0210836 A1 Jul. 27, 2017

(30) Foreign Application Priority Data

Jan. 25, 2016 (JP) ................................ 2016-011349

(51) Int. Cl.

*G03F 7/004* (2006.01)
*C08F 212/14* (2006.01)
(Continued)

(52) U.S. Cl.

CPC .......... *C08F 212/14* (2013.01); *C07C 381/12* (2013.01); *C08F 220/18* (2013.01);
(Continued)

(58) Field of Classification Search

CPC ...... G03F 7/004; G03F 7/0045; G03F 7/0046; G03F 7/0382; G03F 7/20; C08F 220/18; C08F 220/24; C08F 220/30; C07C 381/12
(Continued)

(56) References Cited

U.S. PATENT DOCUMENTS 5,286,600 A 2/1994 Ochiai et al.
5,618,892 A 4/1997 Furihata et al.
(Continued)

FOREIGN PATENT DOCUMENTS

EP 2362267 A1 8/2011
EP 2626743 A1 8/2013
(Continued)

OTHER PUBLICATIONS

Machine Translation of JP 2008-249951 (no date).*
(Continued)

*Primary Examiner* — Amanda C Walke
(74) *Attorney, Agent, or Firm* — Oliff PLC

(57) ABSTRACT

The present invention provides a polymer compound containing a repeating unit shown by the following general formula (1). There can be provided a polymer compound
(Continued)

usable in a negative resist composition that can achieve high resolution of 50 nm or less and small LER and cause very few defects, a negative resist composition using the polymer compound, and a patterning process using the negative resist composition.

(1)

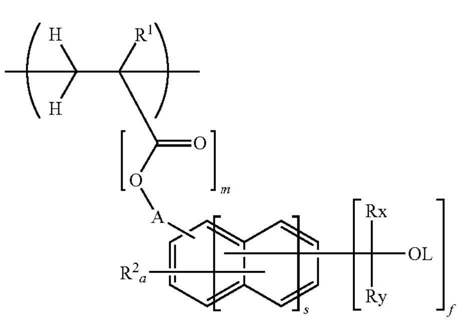

20 Claims, 1 Drawing Sheet

(51) Int. Cl.

| | |
|---|---|
| ***C08F 220/30*** | (2006.01) |
| ***G03F 7/038*** | (2006.01) |
| ***C08F 220/24*** | (2006.01) |
| ***C08F 220/18*** | (2006.01) |
| ***C07C 381/12*** | (2006.01) |
| ***G03F 1/00*** | (2012.01) |

(52) U.S. Cl.

CPC .......... *C08F 220/24* (2013.01); *C08F 220/30* (2013.01); *G03F 1/00* (2013.01); *G03F 7/0045* (2013.01); *G03F 7/0046* (2013.01); *G03F 7/038* (2013.01); *G03F 7/0382* (2013.01); *C08F 2220/301* (2013.01); *C08F 2500/03* (2013.01); *C08F 2800/10* (2013.01)

(58) Field of Classification Search

USPC ........ 430/5, 270.1, 322, 325, 329, 927, 942; 526/243, 319, 326, 281

See application file for complete search history.

(56) References Cited

U.S. PATENT DOCUMENTS

| | | | | |
|---|---|---|---|---|
| 6,506,534 | B1 | 1/2003 | Nozaki et al. | |
| 7,300,739 | B2 | 11/2007 | Allen et al. | |
| 7,393,624 | B2 | 7/2008 | Allen et al. | |
| 7,563,558 | B2 | 7/2009 | Allen et al. | |
| 8,426,109 | B2 * | 4/2013 | Kanda ................... | G03F 7/0045 430/270.1 |
| 8,815,491 | B2 * | 8/2014 | Masunaga ............. | G03F 7/0045 430/270.1 |
| 8,828,643 | B2 * | 9/2014 | Kobayashi ............ | G03F 7/0045 430/270.1 |
| 9,023,587 | B2 * | 5/2015 | Hatakeyama ........... | G03F 7/322 430/270.1 |
| 9,182,670 | B2 * | 11/2015 | Masunaga ............. | G03F 7/0045 |
| 9,188,865 | B2 * | 11/2015 | Yokokawa ............ | G03F 7/0392 |
| 9,244,347 | B2 * | 1/2016 | Komuro ................ | C07C 381/12 |
| 9,244,348 | B2 * | 1/2016 | Masunaga ............. | G03F 7/0382 |
| 9,316,912 | B2 * | 4/2016 | Kobayashi .............. | C07C 69/54 |
| 9,316,915 | B2 * | 4/2016 | Hatakeyama ......... | G03F 7/2037 |
| 9,335,632 | B2 * | 5/2016 | Hatakeyama ........... | G03F 7/039 |
| 9,645,493 | B2 * | 5/2017 | Domon ................. | G03F 7/0045 |
| 2008/0118860 | A1 | 5/2008 | Harada et al. | |
| 2008/0241751 | A1 | 10/2008 | Takeda et al. | |
| 2008/0305411 | A1 | 12/2008 | Koitabashi et al. | |
| 2010/0009299 | A1 | 1/2010 | Watanabe et al. | |
| 2010/0304301 | A1 | 12/2010 | Tanaka et al. | |
| 2011/0287234 | A1 * | 11/2011 | Tsuchihashi ............ | G03F 7/325 428/195.1 |
| 2013/0209922 | A1 | 8/2013 | Masunaga et al. | |

FOREIGN PATENT DOCUMENTS

| | | | | |
|---|---|---|---|---|
| JP | H05-232702 | A | 9/1993 | |
| JP | H08-202037 | A | 8/1996 | |
| JP | 2001-154357 | A | 6/2001 | |
| JP | 2001-226430 | A | 8/2001 | |
| JP | 2003-337414 | A | 11/2003 | |
| JP | 3790649 | B2 | 6/2006 | |
| JP | 2008-111103 | A | 5/2008 | |
| JP | 2008-249762 | A | 10/2008 | |
| JP | 2008249951 | A * | 10/2008 | ........... G03F 7/0045 |
| JP | 2008-304590 | A | 12/2008 | |
| JP | 2010-164933 | A | 7/2010 | |
| JP | 2010-276910 | A | 12/2010 | |
| JP | 2013-164588 | A | 8/2013 | |

OTHER PUBLICATIONS

Yoshida, Masahiro et al., "Cationic chemistry and chemically amplified resist materials for microlithography: synthesis and applications of copolymers of 4-(1-hydroxy-1-methylethyl) styrene and styrene or 4-hydroxystyrene.", Polymer, vol. 35, pp. 5-13, (1994).

Ito, H. et al., "Acid-Catalyzed Dehydration, A New Mechanism for Chemically Amplified Lithographic Imaging.", American Chemical Society, Chapter 5, pp. 64-87, (1994).

Ito, H. et al., "Negative Resist Compositions.". IBM Technical Disclosure Bulletin, vol. 35, No. 1B, p. 397, (1992).

Bozano, Luisa D. et al., "Conductive layer for charge dissipation during electron-beam exposures.", Proc. of SPIE, vol. 8522, (2012).

Jul. 7, 2017 Extended European Search Report issued in Patent Application No. 17000111.9.

* cited by examiner

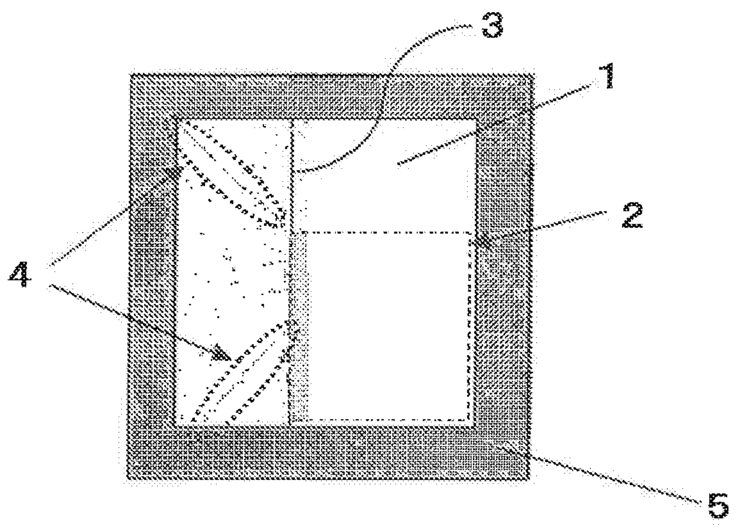
3
1
2
4
5

POLYMER COMPOUND, NEGATIVE RESIST COMPOSITION, LAMINATE, PATTERNING PROCESS, AND COMPOUND

BACKGROUND OF THE INVENTION

Field of the Invention

The present invention relates to a polymer compound and a negative resist composition, particularly a negative resist composition using a polymer compound that has a polarity inversion function used for processing a semiconductor substrate or a photomask substrate, and also relates to a laminate and a patterning process using the same, and a compound.

Description of the Related Art

It is well known that a finer pattern rule is required for LSI with higher integration and higher processing speed. Exposure methods and resist compositions significantly vary accordingly. Especially in lithography of a 0.2-μm or less pattern, KrF excimer laser beam, ArF excimer laser beam, electron beam, or the like is used as the exposure light source, and a chemically amplified resist composition having a good sensitivity to such high energy beams and a high resolution is used as the photoresist composition.

The resist composition can be classified into a positive type, in which an exposed part dissolves, and a negative type, in which an exposed part remains as a pattern. The more useful one is selected according to a resist pattern to be required. A chemically amplified negative resist composition generally contains a polymer that can dissolve in an aqueous alkaline developer, an acid generator that can decompose by photo-exposure and generate acid, and a crosslinking agent that can crosslink the polymer by using the acid as a catalyst and then insolubilize the polymer in the developer (the polymer and the crosslinking agent can be integrated). In addition, a basic compound for controlling diffusion of the acid generated by the exposure is usually added thereto.

Many negative resist compositions using a phenol unit as an alkali-soluble unit constituting the polymer compound that can dissolve in an aqueous alkaline developer have been investigated for exposure especially with KrF excimer laser beam. These negative resist compositions have not been used for ArF excimer laser beam because the phenol unit has no transmittance to an exposure light with a wavelength of 150 to 220 nm. However, they have recently received a growing technical attention as negative resist compositions for EB and EUV exposure, which are used in an exposure method for forming a finer pattern, and examples thereof are proposed in Patent Documents 1, 2 and 3 as resist compositions that exhibit very high resolution even when the compositions are used for forming a thin film.

In addition to the above compositions, many materials have been investigated for the chemically amplified negative resist. For example, many crosslinking agents have been investigated to insolubilize an alkali-soluble polymer used in the resist composition that provides the negative mechanism by an effect of acid generated at the irradiation with a high energy beam, as used in Patent Documents 1, 2 and 3. On the other hand, there are various attempts to make a polymer having a function of crosslinking agent, and the following methods have been proposed: a method of introducing a styrene unit substituted with an alkoxymethoxy group (Patent Document 4); a method of introducing a repeating unit having an alkoxymethylamino group (Patent Document 5); a method of introducing a repeating unit having an epoxy group (Patent Document 6); a method of introducing a styrene repeating unit having an acid-labile group (Patent Document 7); a method of introducing an adamantyl repeating unit having an acid-labile hydroxyl group (Patent Document 8); a method of introducing an aliphatic hydrocarbon or alicyclic hydrocarbon repeating unit having an acid-labile hydroxyl group (Patent Documents 9, 10, and 11). Examples of the materials having an acid-labile hydroxyl group are proposed in Non-Patent Documents 1, 2, and 3.

PRIOR ART DOCUMENTS

Patent Documents

Patent Document 1: Japanese Patent Laid-Open Publication No. 2010-276910

Patent Document 2: Japanese Patent Laid-Open Publication No. 2010-164933

Patent Document 3: Japanese Patent Laid-Open Publication No. 2008-249762

Patent Document 4: Japanese Patent Laid-Open Publication No. H05-232702

Patent Document 5: Japanese Patent Laid-Open Publication No. H08-202037

Patent Document 6: Japanese Patent Laid-Open Publication No. 2001-226430

Patent Document 7: Japanese Patent Laid-Open Publication No. 2003-337414

Patent Document 8: Japanese Patent Laid-Open Publication No. 2001-154357

Patent Document 9: U.S. Pat. No. 7,300,739

Patent Document 10: U.S. Pat. No. 7,393,624

Patent Document 11: U.S. Pat. No. 7,563,558

Patent Document 12: Japanese Patent Laid-Open Publication No. 2013-164588

Non-Patent Documents

Non-Patent Document 1: H. Ito, and R. Sooriyakumaran, IBM Technical Disclosure Bulletin Vol. 35, No. 1B, 397 (1992)

Non-Patent Document 2: H. Ito, Y. Maekawa, R. Sooriyakumaran, and E. A. Mash, ACS Symposium Series 537, Chapter 5, pp 64-87 (1994)

Non-Patent Document 3: M. Yoshida, and J. M. J. Frechet, Polymer, 35 (1), 5 (1994)

SUMMARY OF THE INVENTION

As finer patterning is required, the resist composition is required to have excellent limiting resolution, small LER (line edge roughness), and low temperature dependence. In addition to these, another significant factor is that no defects occur. In particular, a resist composition for electron beam, which is often used in mask blank processing, put an emphasis on that no defects occur. The reason is that a semiconductor device manufactured by transferring a pattern on a mask processed with the electron beam resist composition to a wafer may have defects caused at patterning of the electron beam resist composition. If the defects remain on the mask, the defects are transferred to the wafer, reducing a yield of semiconductor devices.

A resist composition disclosed in Patent Document 12 can improve the resolution and remedy the pattern density dependence, but is unsatisfactory in the defect performance. More specifically, this resist composition has been found to cause many defects that are radially distributed from a patterning portion when subjected to patterning and then development.

FIG. 1 is an explanatory view of the defects radially distributed from a patterning portion (a radial defect). The radial defect will now be specifically described with reference to this explanatory view. In FIG. 1, the reference number 1 denotes a blank substrate, 2 denotes a portion on which a line and space pattern is drawn, 3 denotes a position at which the number of detected defects reaches a limit, 4 denotes the radial defect, and 5 denotes a background.

First, a line and space pattern is drawn on the blank substrate 1 (at the portion 2 in FIG. 1). After drawing, development is performed, and defects are inspected on the entire blank substrate 1 from the left side. At the position 3 in FIG. 1, the number of detected defects (development defects, shown by dots in the blank substrate 1) reaches a limit of the inspection apparatus, and the inspection is terminated. At this time, a defect that extends outwardly from the center of the blank substrate 1 is observed in the inspected area (i.e., the left area from the position 3 in FIG. 1); this defect is referred to as the radial defect 4.

An object of the present invention is to provide a polymer compound for use in a negative resist composition that can achieve high resolution of 50 nm or less and small LER and cause very few defects, a negative resist composition using the polymer compound, and a patterning process using the negative resist composition.

To achieve the above object, the present invention provides a polymer compound comprising a repeating unit shown by the following general formula (1), (1)

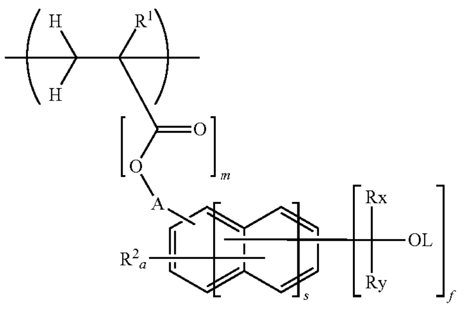

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents an integer of 0 to 2; "a" represents an integer of 5+2s−f; "m" represents 0 or 1; Rx and Ry represent a hydrogen atom or a substituent shown by the following (i) or (ii), provided that Rx and Ry are not a hydrogen atom at the same time:

(i) a monovalent aromatic group optionally containing a substituent;

(ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms.

This polymer compound can provide a negative resist composition that can achieve high resolution of 50 nm or less and small LER and cause very few defects.

The polymer compound preferably further comprises one or more of a repeating unit shown by the following general formula (2) and a repeating unit shown by the following general formula (3), (2)

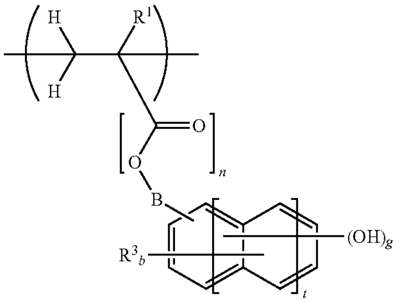

(3)

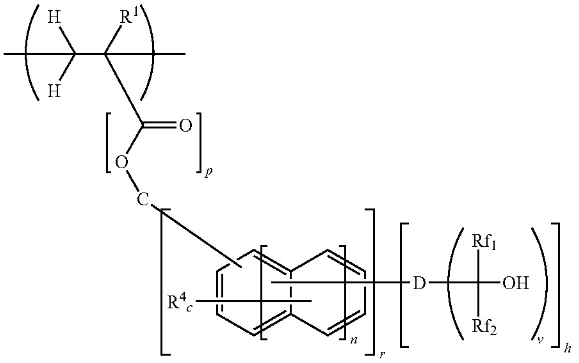

wherein B and C represent a single bond or an alkylene group having 1 to 10 carbon atoms and optionally containing an ether oxygen atom in a chain of the alkylene group; D represent a single bond or a linear, branched, or cyclic v+1-valent aliphatic hydrocarbon group optionally substituted with a fluorine atom and optionally containing an ether oxygen atom, a carbonyl group, or a carbonyloxy group in a chain of the hydrocarbon group; $R^1$ represents a hydrogen atom, a fluorine atom, a methyl group, or a trifluoromethyl group; $R^3$ and $R^4$ independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; $Rf_1$ and $Rf_2$ represent an alkyl group having 1 to 6 carbon atoms and at least one fluorine atom, and $Rf_1$ and D may be bonded to form a ring together with the carbon atom to which $Rf_1$ and D are bonded; "g" represents an integer of 0 to 3; "h"

represents 1 or 2; "r" represents 0 or 1; "v" represents 1 or 2; "t" and "u" represent an integer of 0 to 2; "b" represents an integer of 5+2t−g; "c" represents an integer of 5+2u−h; and "n" and "p" independently represent 0 or 1, provided that when "r" is 0, "p" is 1 and C is a single bond.

This polymer compound can effectively promote the insolubilization reaction with elimination of the acid-labile group contained in the repeating unit of formula (1) and thus provide a negative resist composition having higher resolution.

The polymer compound preferably further comprises one or more of a repeating unit shown by the following general formula (4) and a repeating unit shown by the following general formula (5), (4)

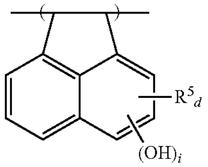

(5)

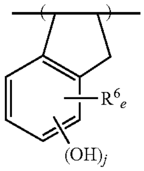

wherein $R^5$ and $R^6$ independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; "i" and "j" represent an integer of 0 to 3; "d" represents an integer of 0 to 5; and "e" represents an integer of 0 to 3.

A resist film obtained from a negative resist composition using this polymer compound can significantly inhibit pattern dependence on dimension of an irradiated pattern and a pattern to be formed even when a pattern exposure including both an isolated pattern and an isolated space pattern is performed with electron beam or EUV, as well as the resist film can have high resolution.

The polymer compound preferably further comprises one or more of a repeating unit shown by the following general formula (a1), a repeating unit shown by the following general formula (a2), and a repeating unit shown by the following general formula (a3), (a1)

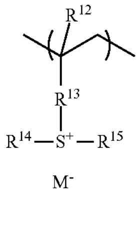

-continued (a2)

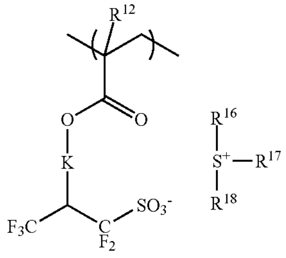

(a3)

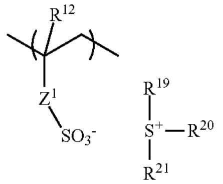

wherein $R^{12}$ independently represents a hydrogen atom or a methyl group; $R^{13}$ represents a single bond, a phenylene group, $—O—R^{22}—$, or $—C(═O)—Z^2—R^{22}—$, where $Z^2$ represents an oxygen atom or NH, and $R^{22}$ represents a phenylene group or a linear, branched, or cyclic alkylene group or alkenylene group having 1 to 6 carbon atoms and optionally containing a carbonyl group, an ester group, an ether group, or a hydroxyl group; K represents a single bond or $—Z^3—C(═O)—$, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, $—O—R^{23}—$, or $—C(═O)—Z^4—R^{23}—$, where $Z^4$ represents an oxygen atom or NH, and $R^{23}$ represents a phenylene group or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

When such repeating units are incorporated in the polymer compound, acid diffusion is appropriately controlled, and a pattern with a reduced LER can be obtained. Moreover, this polymer compound can inhibit a chemical flare phenomenon, where acid is vaporized from an exposed part and reattached to an unexposed part, at baking under vacuum, thus reducing LER and defects due to unexpected inhibition of the negative reaction at the unexposed part.

Furthermore, the present invention provides a negative resist composition comprising the above-mentioned polymer compound.

This negative resist composition can achieve high resolution of 50 nm or less and small LER and cause very few defects.

The negative resist composition preferably further comprises a compound capable of generating acid by irradiation with a high energy beam.

The inventive negative resist composition may contain a compound capable of generating acid by irradiation with a high energy beam.

The negative resist composition preferably further comprises a salt shown by the following general formula (3a), $$R^{11}—CO_2^-Q^+ \quad (3a)$$

wherein $R^{11}$ represents a linear, branched, or cyclic alkyl group having 1 to 20 carbon atoms, alkenyl group having 2 to 20 carbon atoms, aryl group having 6 to 36 carbon atoms, in which these groups optionally contain a fluorine atom, a nitrogen atom, an ether group, an ester group, a lactone ring, a lactam ring, a carbonyl group, or a hydroxyl group; Q represents a counter cation having a substituent selected from a sulfonium cation, an iodonium cation, and an ammonium cation.

This negative resist composition is not affected by heat generated at baking and drawing and can reduce the temperature dependence on the pattern dimension.

Furthermore, the present invention provides a laminate comprising the above-mentioned resist film formed from the negative resist composition on a photomask blank.

This laminate can be successfully coated with an antistatic film.

Furthermore, the present invention provides a patterning process comprising the steps of: forming a resist film from the above-mentioned negative resist composition on a substrate to be processed; pattern-irradiating the resist film with a high energy beam; and developing the resist film with an alkaline developer to form a resist pattern.

This patterning process can form a pattern having very few defects with high resolution of 50 nm or less and small LER.

The high energy beam is preferably an EUV or an electron beam.

The above-mentioned high energy beam can be employed in the inventive patterning process.

The substrate to be processed is preferably a photomask blank.

In this manner, a photomask having a pattern with extremely high resolution, small LER, and excellent rectangularity can be produced.

An outermost surface of the photomask blank is preferably formed of a chromium material.

In this manner, a chromium material can be used in the outermost surface of the photomask blank in the inventive patterning process.

Furthermore, the present invention provides a compound shown by the following general formula (1a), (1a)

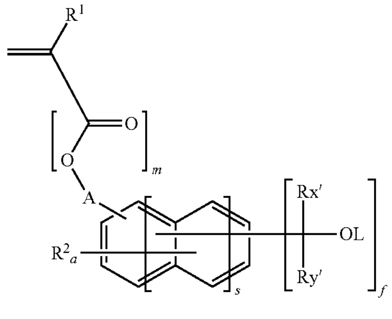

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents an integer of 0 to 2; "a" represents an integer of 5+2s−f; "m" represents 0 or 1; Rx' and Ry' represent a hydrogen atom, or an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx' and Ry' and directly bonded to the carbon atom bonded to Rx' and Ry' are not bonded to hydrogen atoms, and Rx' and Ry' are not a hydrogen atom at the same time.

The inventive polymer compound can be obtained by using this compound.

As mentioned above, the present invention provides a polymer compound for use in a negative resist composition that can achieve high resolution of 50 nm or less and small LER and cause very few defects, as well as a negative resist composition using the polymer compound. The inventive negative resist composition can provide a pattern having extremely high resolution and small LER in a fine processing technique, especially an electron beam lithography. Moreover, the inventive negative resist composition, which uses the polymer compound containing a repeating unit with a specific partial structure, can inhibit the defect occurrence, and thus is useful for processing, particularly, a mask blank. Moreover, the inventive laminate can be successfully coated with an antistatic film. Moreover, the inventive patterning process can form a pattern having very few defects with high resolution of 50 nm or less and small LER.

BRIEF DESCRIPTION OF THE DRAWING

FIG. 1 is an exemplary view of defects (radial defect) that are radially distributed from a patterning portion after development.

DETAILED DESCRIPTION OF THE PREFERRED EMBODIMENTS

As mentioned above, it is desired to develop a polymer compound for use in a negative resist composition that can achieve high resolution of 50 nm or less and small LER and cause very few defects.

To accomplish the object, the present inventors have diligently studied to develop a high-resolution negative resist composition containing a polymer compound (a polymer) that has a cyclic olefin unit with an aromatic ring and an acid-labile hydroxyl group or alkoxy group unit in its side chain, proposed in Patent Document 12.

As part of the studies, they synthesized polymers that have different units containing an acid-labile hydroxyl group or an alkoxy group, and evaluated defects of negative resist compositions. They consequently found that the defects can be significantly inhibited by a negative resist composition using a polymer having a repeating unit not containing hydrogen atoms that produce water through beta-elimination reaction with hydroxyl groups in the presence of acid, thereby bringing the present invention to completion.

That is, the present invention is a polymer compound comprising a repeating unit shown by the following general formula (1), (1)

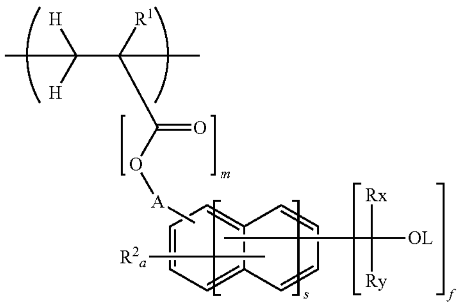

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents an integer of 0 to 2; "a" represents an integer of 5+2s−f; "m" represents 0 or 1; Rx and Ry represent a hydrogen atom or a substituent shown by the following (i) or (ii), provided that Rx and Ry are not a hydrogen atom at the same time:

(i) a monovalent aromatic group optionally containing a substituent;

(ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms.

Hereinafter, the present invention will be described in detail, but the present invention is not limited thereto.

In the present invention, Me denotes a methyl group.

Further, in the present invention, a carbonyl group is —CO—, an ester bond is —COO—, and an ether group is —O—.

[Compound]

The present invention provides a compound shown by the following general formula (1a), (1a)

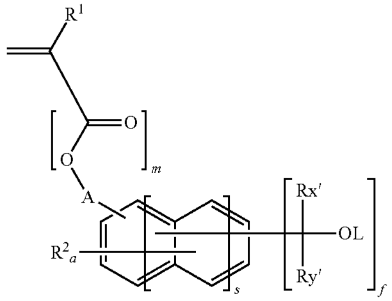

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents an integer of 0 to 2; "a" represents an integer of 5+2s−f; "m" represents 0 or 1; Rx' and Ry' represent a hydrogen atom, or an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx' and Ry' and directly bonded to the carbon atom bonded to Rx' and Ry' are not bonded to hydrogen atoms, and Rx' and Ry' are not a hydrogen atom at the same time.

This compound is a monomer to give a later-described repeating unit shown by the general formula (1) where Rx and Ry are a hydrogen atom or (ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms. Preferable examples of the compound include the following compounds.

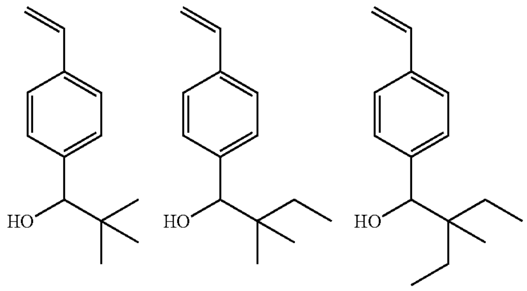

-continued
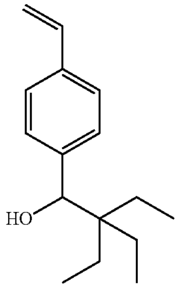
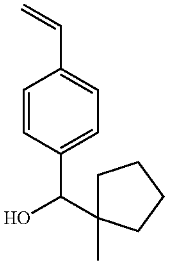
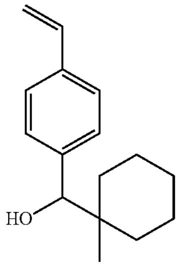
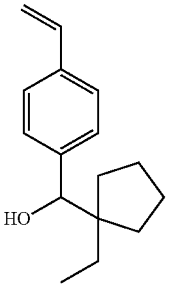
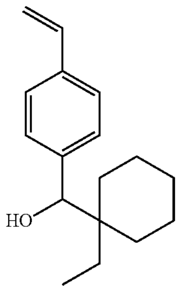
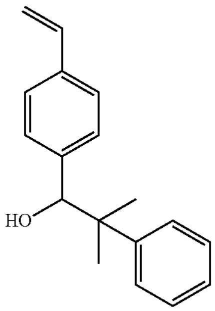
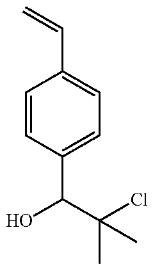
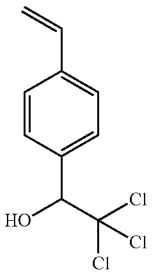
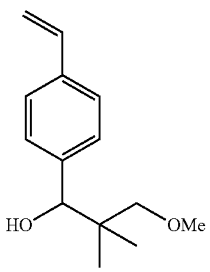
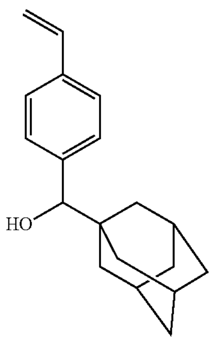
-continued
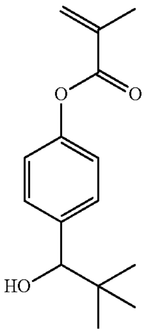
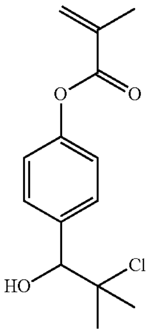
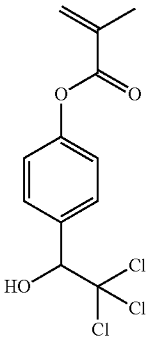
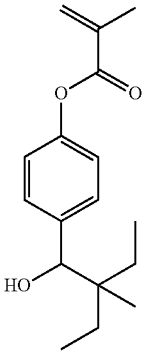
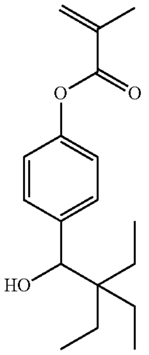
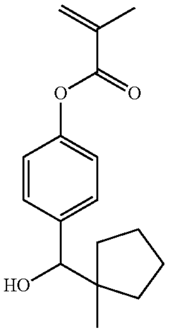
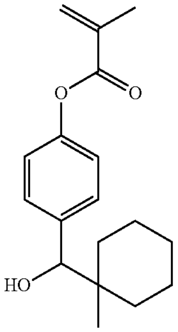
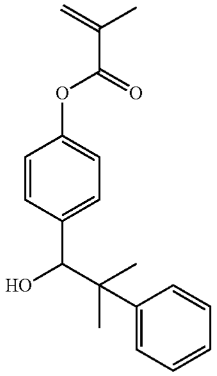
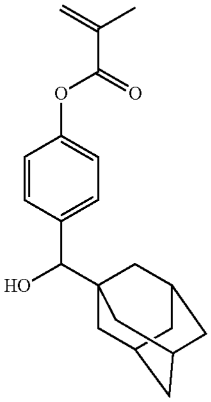
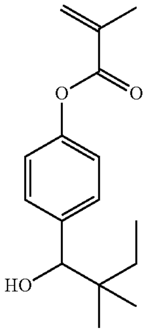
(Method of Producing Compound)
The following scheme shows an exemplary method of producing the above compound in which $R^1$ is a hydrogen atom, “m” is 0, “f” is 1, L is a hydrogen atom, and A is a single bond, although the method is not limited thereto.

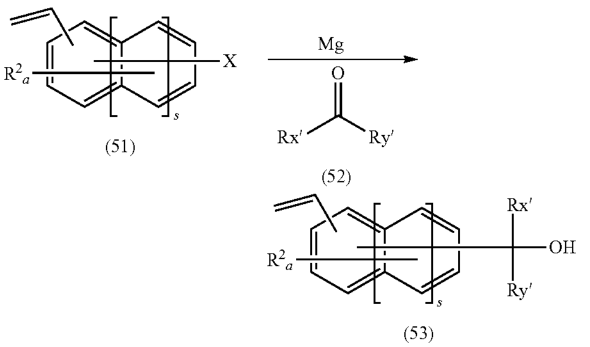

(51) (52) (53)

wherein $R^2$, "a", "s", Rx' and Ry' are as defined above; and X represents a halogen atom.

The above reaction is carried out by preparing a Grignard reagent of halovinylarene (51) and subjecting the reagent to nucleophilic addition to a carbonyl compound (52). The reaction mixture is then subjected to a usual aqueous post-treatment (aqueous work-up) to obtain a monomer (53). If necessary, the monomer may be purified according to a conventional method, such as distillation, recrystallization, or chromatography.

The following scheme is case of a compound in which "m" is 1, "f" is 1, L is a hydrogen atom, and A is a single bond, although the method is not limited thereto.

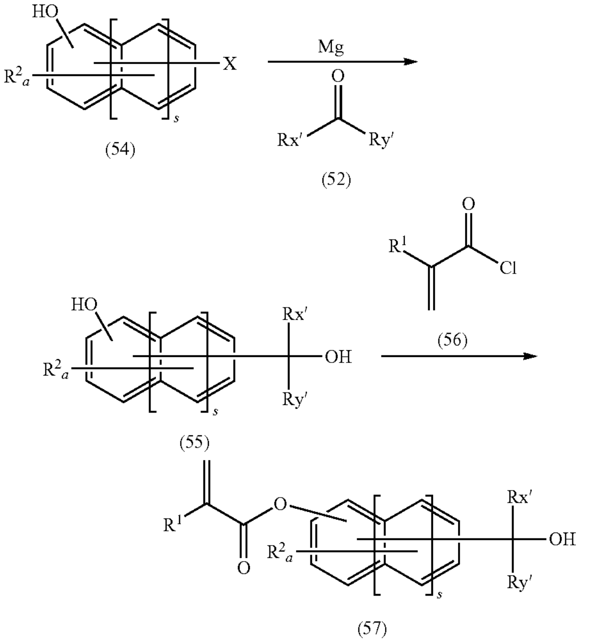

(54) (52) (56) (55) (57)

wherein $R^1$, $R^2$, "a", "s", Rx', Ry' and X are as defined above.

In the above reaction, firstly, a Grignard reagent of halophenol (54) is prepared, and the reagent is subjected to nucleophilic addition to a carbonyl compound (52), followed by optional purification according to a conventional method, such as distillation, recrystallization, or chromatography to obtain phenol (55). The obtained phenol (55) undergoes reaction with an acylating agent (56) to obtain a monomer (57). This reaction easily proceeds according to a known method. Moreover, this reaction is preferably performed without a solvent or in a solvent such as methylene chloride, toluene, hexane, diethyl ether, tetrahydrofuran, or acetonitrile, by mixing the phenol (55) with the acylating agent and a base such as triethylamine, pyridine, or 4-dimethylaminopyridine successively or collectively, under cooling or heating as needed. If necessary, the monomer may be purified according to a conventional method, such as distillation, recrystallization, or chromatography.

[Polymer Compound]

The present invention provides a polymer compound containing a repeating unit shown by the following general formula (1), (1)

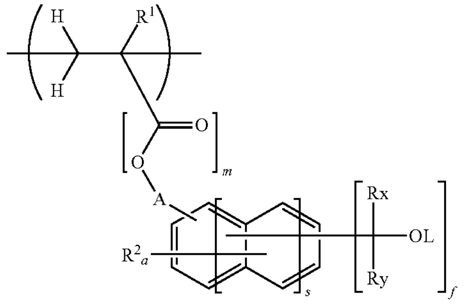

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents an integer of 0 to 2; "a" represents an integer of 5+2s−f; "m" represents 0 or 1; Rx and Ry represent a hydrogen atom or a substituent shown by the following (i) or (ii), provided that Rx and Ry are not a hydrogen atom at the same time:

(i) a monovalent aromatic group optionally containing a substituent;

(ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms.

The aromatic ring is substituted with the side chain having the acid-labile group, in which the substitution number "f" is an integer of 1 to 3. L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent. Illustrative examples thereof include a hydrogen atom, a methyl group, an ethyl group, a propyl group, an isopropyl group, a cyclopentyl group, a cyclohexyl group, an adamantyl group, a methylcarbonyl group, and a phenyl group.

The aromatic ring shown in the general formula (1) may be bonded to the main chain by a single bond, or may be bonded via a carbonyloxy group and further a linker A. "s" represents an integer of 0 to 2. When "s" is 0, 1, or 2, the aromatic ring shown in the general formula (1) is a benzene ring, a naphthalene ring, or an anthracene ring, respectively.

A represents a single bond or an alkylene group having 1 to 10 carbon atoms and optionally containing an ether oxygen atom (an ether bond) in a chain of the alkylene group. Preferable examples of the alkylene group include a methylene group, an ethylene group, a propylene group, a butylene group, a pentylene group, a hexylene group, and structural isomers having a carbon skeleton with branched or cyclic structure. In the case that ether oxygen is contained and "m" in the formula (1) is 1, the ether oxygen may be at any position except the position between α-carbon and β-carbon relative to the ester oxygen. When "m" is 0, the atom bonding to the main chain is the ether oxygen, and second ether oxygen may be contained at any position except the position between α-carbon and β-carbon relative to the first ether oxygen.

$R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen. Illustrative examples thereof include a hydrogen atom, a methyl group, an ethyl group, a propyl group, a methoxy group, an ethoxy group, a propoxy group, and an isopropoxy group; in particular, a hydrogen atom is preferable.

Once the repeating unit shown by the general formula (1) is irradiated with a high energy beam, the acid-labile group (the —OL group) is removed by an effect of acid generated by an acid generator, and a benzyl cation is produced. The benzyl cation induces crosslinking reaction in the polymer and thus insolubilizes the polymer in an alkaline developer. Consequently, the part irradiated with the high energy beam becomes negative. By contrast, the polymer compound containing 4-(2-hydroxy-2-propyl)styrene units disclosed in Patent Document 12 has hydrogen atoms that produce water through β-elimination reaction with acid-labile groups (hydroxyl groups in this case). This causes dehydration reaction to produce olefin, besides the reaction to produce the benzyl cation. The polymer that has produced the olefin (hereinafter, referred to as a dehydrated polymer) has less solubility in an alkaline developer than that of the undehydrated polymer due to the loss of hydroxyl groups, but still has a little solubility. Thus, the dehydrated polymer is slightly dissolved from the exposed part during development while its dissolution rate is very low. Generally, the development is performed by supplying a developer to a rotated substrate. However, because the dissolution rate is very low, the dehydrated polymer cannot be completely removed by the developer, and a trace of the dehydrated polymer remains on the substrate at completion of the development. As a result, the radial defect occurs from the center of the substrate.

The inventive polymer compound has a structure that does not cause the dehydration reaction and thus undergoes only the crosslinking reaction in the polymer. Therefore, the above-mentioned defect is not caused.

Among the repeating units shown by the general formula (1), preferable examples of the repeating unit in which Rx and Ry are a hydrogen atom or (i) a monovalent aromatic group optionally containing a substituent are shown below.

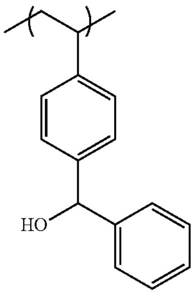
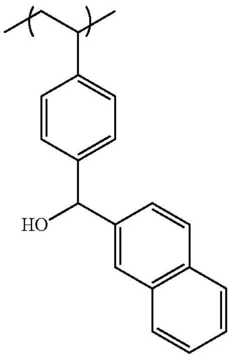
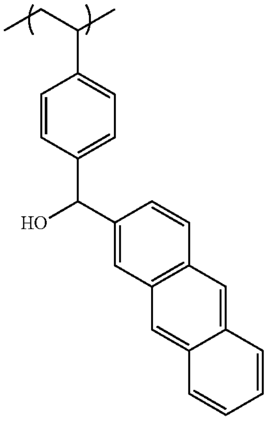
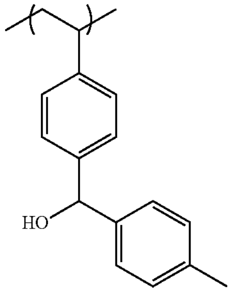
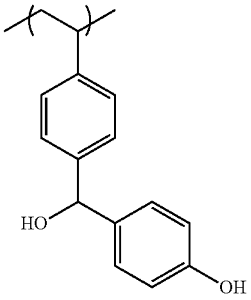
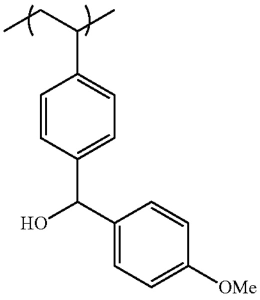
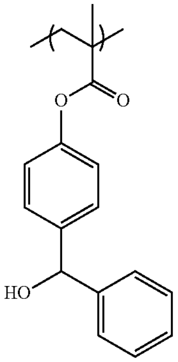
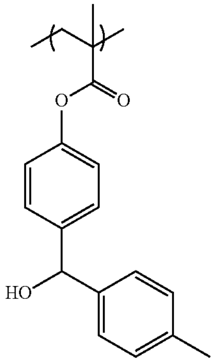

-continued

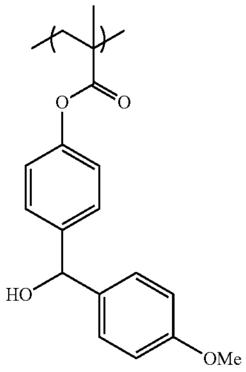

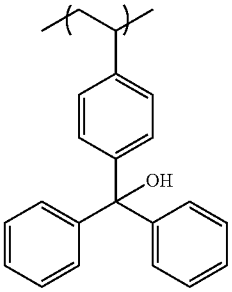

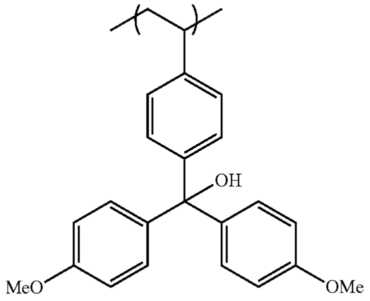

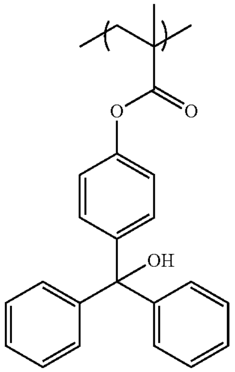

Among the repeating units shown by the general formula (1), preferable examples of the repeating unit in which Rx and Ry are a hydrogen atom or (ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms are shown below.

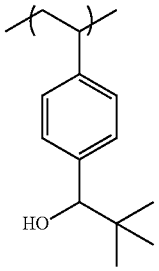

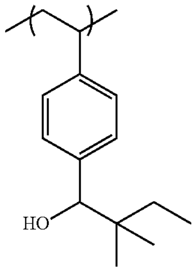

-continued

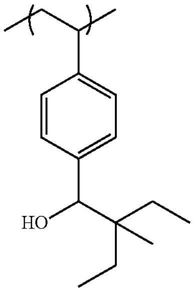

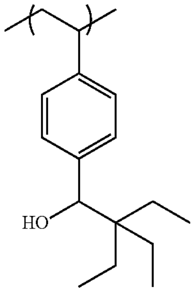

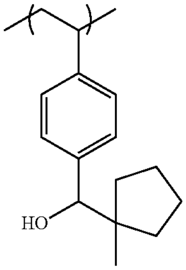

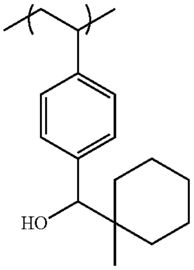

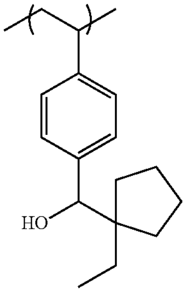

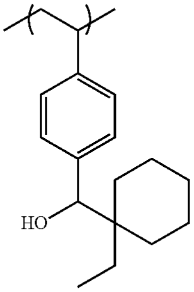

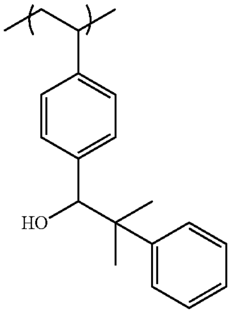

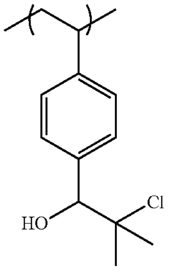

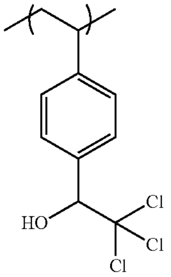

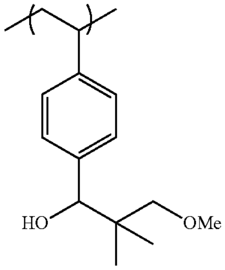

-continued

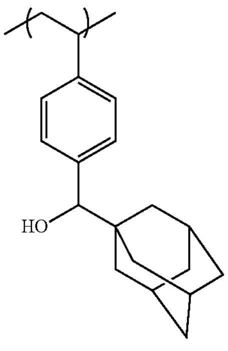
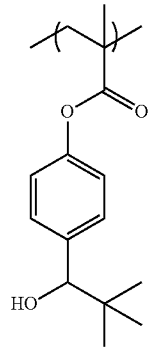
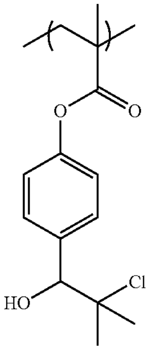
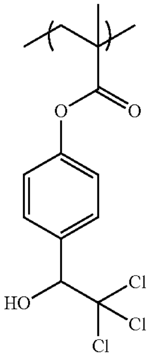
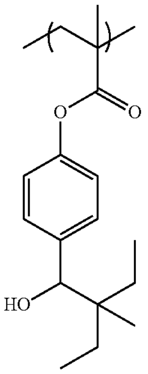
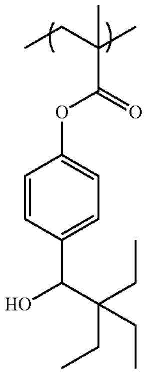
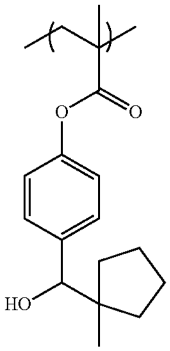
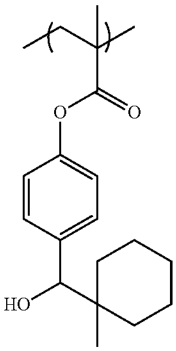
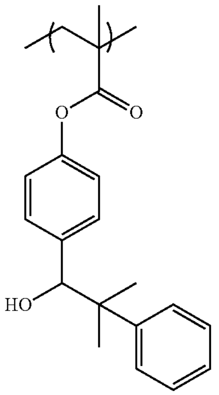

-continued

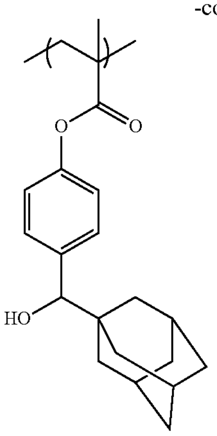
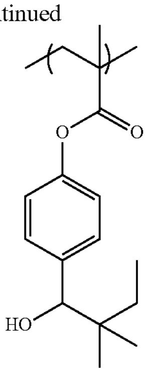

The polymer compound according to the invention preferably contains one or more of a repeating unit shown by the following general formula (2) and a repeating unit shown by the following general formula (3), which are units that allow an appropriate thermal vibration of the polymer compound, to effectively promote the insolubilization reaction with elimination of the acid-labile group contained in the repeating unit shown by the formula (1) and provide a negative resist composition having high resolution.

(2)

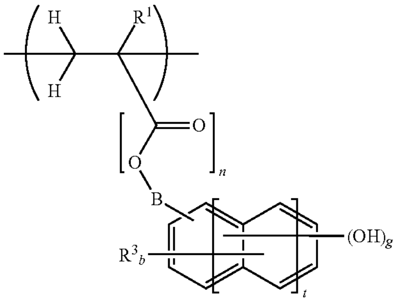

(3)

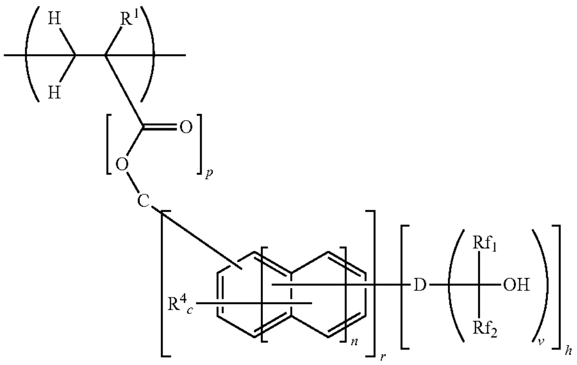

wherein B and C represent a single bond or an alkylene group having 1 to 10 carbon atoms and optionally containing an ether oxygen atom in a chain of the alkylene group; D represent a single bond or a linear, branched, or cyclic v+1-valent aliphatic hydrocarbon group optionally substituted with a fluorine atom and optionally containing an ether oxygen atom, a carbonyl group, or a carbonyloxy group in a chain of the hydrocarbon group; $R^1$ represents a hydrogen atom, a fluorine atom, a methyl group, or a trifluoromethyl group; $R^3$ and $R^4$ independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; $Rf_1$ and $Rf_2$ represent an alkyl group having 1 to 6 carbon atoms and at least one fluorine atom, and $Rf_1$ and D may be bonded to form a ring together with the carbon atom to which $Rf_1$ and D are bonded; "g" represents an integer of 0 to 3; "h" represents 1 or 2; "r" represents 0 or 1; "v" represents 1 or 2; "t" and "u" represent an integer of 0 to 2; "b" represents an integer of 5+2t−g; "c" represents an integer of 5+2u−h; and "n" and "p" independently represent 0 or 1, provided that when "r" is 0, "p" is 1 and C is a single bond.

In the general formula (2), $R^1$ has the same meaning as in the general formula (1), and $R^3$ and "b" have the same meanings as $R^2$ and "a" in the general formula (1). Preferable examples thereof are also the same as them. Moreover, the linker B has the same meaning as A in the general formula (1), and preferable examples thereof are also the same.

Although "g" in the general formula (2), which represents the number of hydroxyl groups substituted for the aromatic ring, is an integer of 0 to 3, the polymer compound contained in the negative resist composition preferably contains a repeating unit having a phenolic hydroxyl group or the repeating unit shown by the general formula (3) to obtain solubility in an aqueous alkaline developer and substrate adhesion, as described later. In addition, the polymer compound preferably contains a repeating unit of formula (2) in which "g" is 1 or more, more preferably 50 mol % or more of the unit of formula (2) in which "g" is 1 or more. The reason is that such a repeating unit has high activity with respect to the insolubilization reaction with elimination of the acid-labile group contained in the repeating unit shown by the general formula (1), and thus provides high resolution. In addition, a repeating unit in which "g" is 0 may be used to adjust the dissolution rate and tolerance to thermal vibration of the polymer compound, although this unit may be not contained according to the design.

The aromatic ring contained in the general formula (2) may be bonded to the main chain by a single bond, or may be bonded via a carbonyloxy group and further a linker B, like the general formula (1). "t" represents an integer of 0 to 2. When "t" is 0, 1, or 2, the aromatic ring shown in the general formula (2) is a benzene ring, a naphthalene ring, or an anthracene ring, respectively.

Among the repeating units shown by the formula (2), the repeating unit in which "g" is 1 or more, "n" is 0, and B is a single bond, i.e., the repeating unit in which the aromatic ring is directly bonded to the main chain (without a linker) is derived from a monomer in which a 1-position substituted or unsubstituted vinyl group is bonded to an aromatic ring substituted with a hydroxyl group, typified by a hydroxystyrene unit. Preferable examples of this repeating unit include repeating units obtained by polymerizing 3-hydroxystyrene, 4-hydroxystyrene, 5-hydroxy-2-vinyl naphthalene, 6-hydroxy-2-vinyl naphthalene, or the like. More preferable are repeating units obtained by polymerizing 3-hydroxystyrene or 4-hydroxystyrene, shown by the formula (7).

(7)

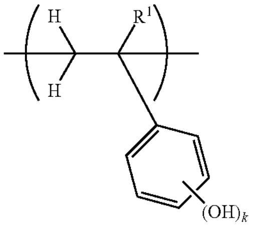

wherein $R^1$ is as defined above; and "k" represents an integer of 1 to 3.

The repeating unit in which "n" is 1, i.e., the repeating unit having an ester skeleton as a linker is a vinyl monomer unit having a substituted carbonyl group, typified by (meth)acrylate.

Preferable examples of the repeating unit shown by the general formula (2) in which "g" is 1 or more and which has a (meth)acrylic acid ester derived linker (—CO—O—B—) are shown below.

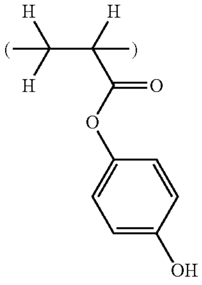

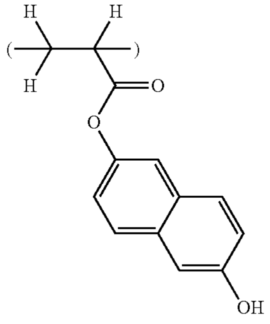

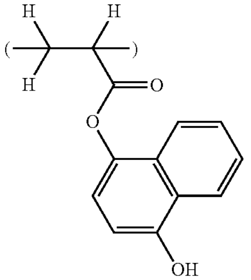

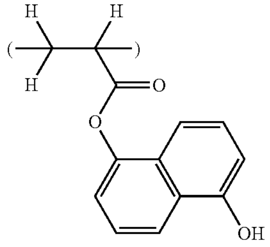

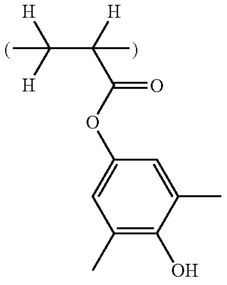

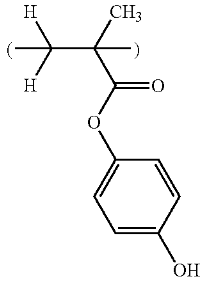

-continued

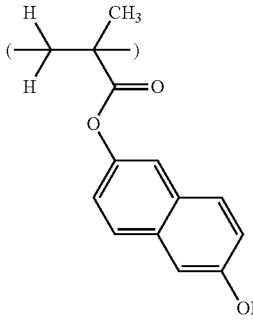

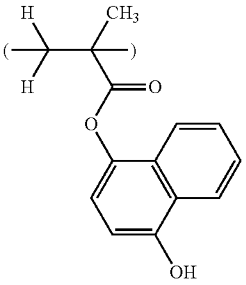

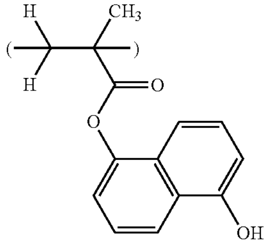

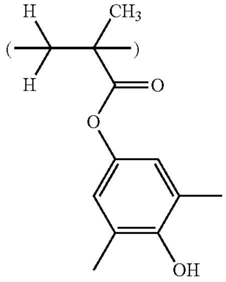

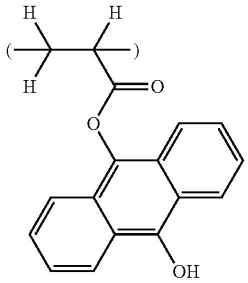

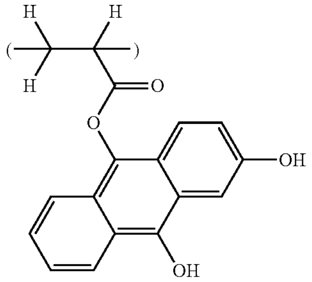

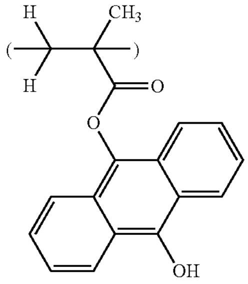

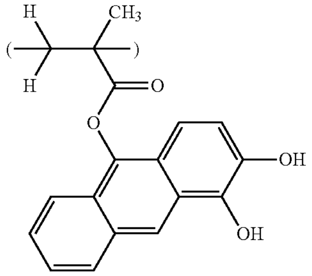

-continued

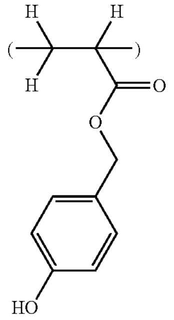

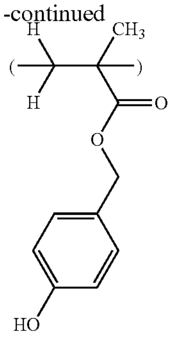

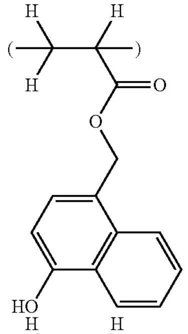

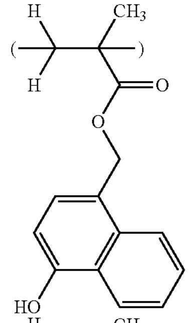

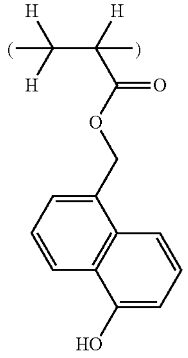

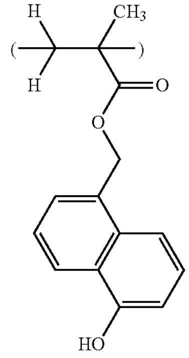

Among the repeating units shown by the formula (2), examples of the repeating unit in which "g" is 0 include repeating units of styrene, vinylnaphthalene, vinylanthracene, or units in which the aromatic ring is substituted with a halogen atom, an acyloxy group, an alkyl group, or an alkoxy group, as described above. Examples of the repeating unit having a (meth)acrylic acid ester derived linker (—CO—O—B—) in which "g" is 0 include repeating units obtained by, with respect to the preferable structure of the repeating units in which "g" is 1 or more, removing hydroxyl groups or substituting hydrogen atoms of the hydroxyl groups with an acyl group or an alkyl group.

In the general formula (3), $R^1$ has the same meaning as in the general formula (1), and $R^4$ and "c" have the same meanings as $R^2$ and "a" in the general formula (1). Preferable examples thereof are also the same as them. Moreover, the linker C has the same meaning as A in the general formula (1), and preferable examples thereof are also the same.

The repeating unit shown by the general formula (3) in which "r" is 1 contains an aromatic ring between the polymer main chain and the hydroxyl group bonded to the carbon adjacent to the fluorinated carbon. "v", which represents the substitution number of D, is 1 or 2. When D is not a single bond, D has one or two hydroxyl groups bonded to the carbon adjacent to the fluorinated carbon.

When "r" is 0, "p" is 1, C is a single bond, and D is bonded to the polymer main chain via a carbonyloxy group.

Also in this case, D has one or two hydroxyl groups bonded to the carbon adjacent to the fluorinated carbon.
Preferable examples of the repeating unit shown by the general formula (3) are shown below, although not limited thereto.
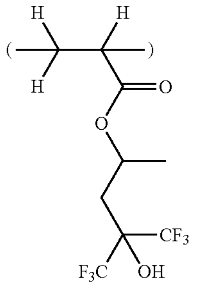
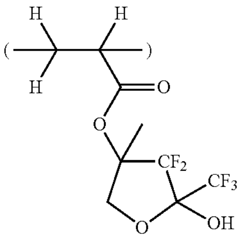
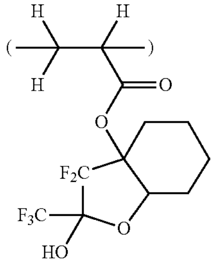
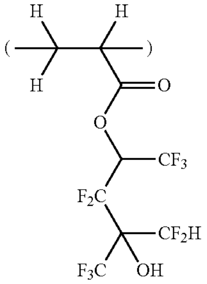
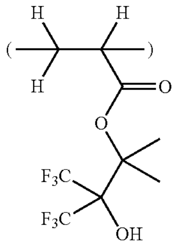
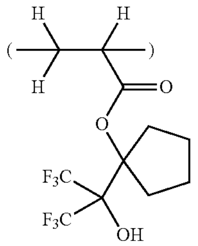
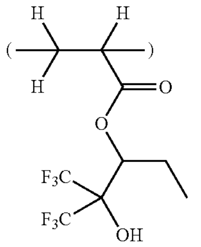
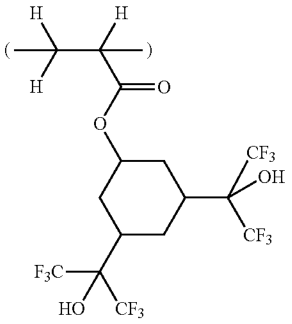
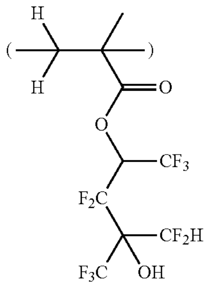
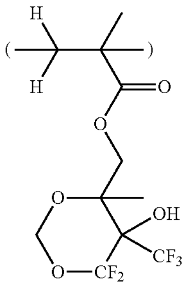
-continued
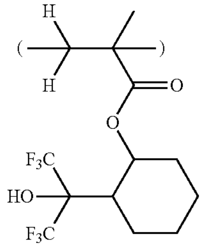
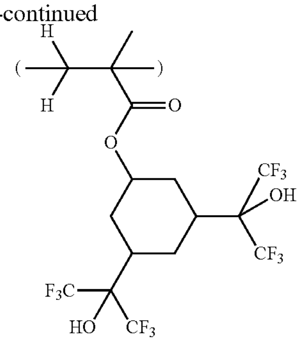
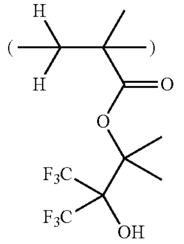
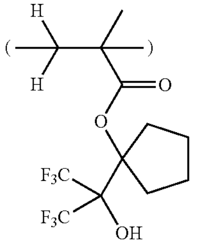
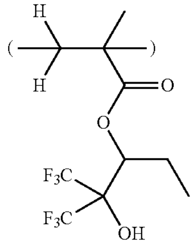
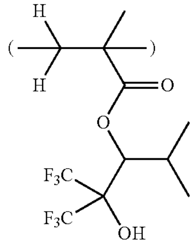
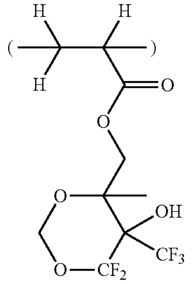
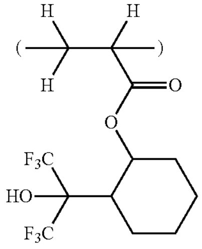
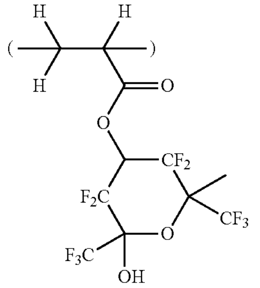
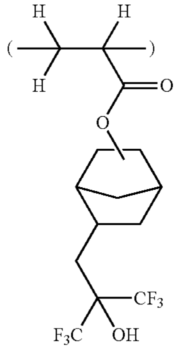
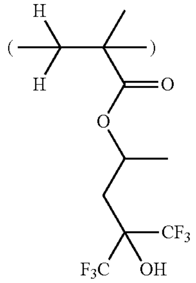
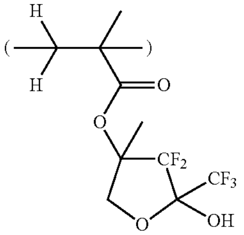

-continued

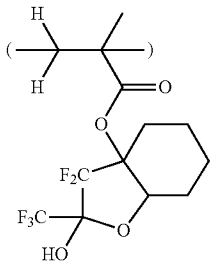

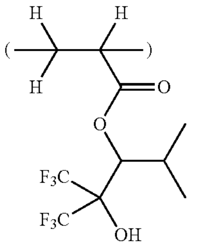

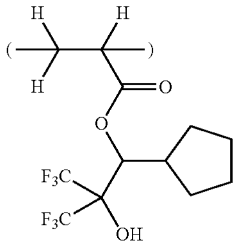

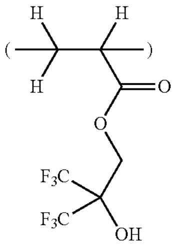

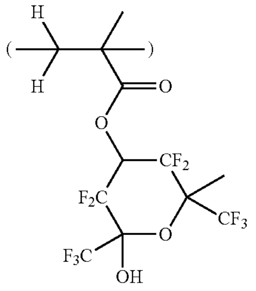

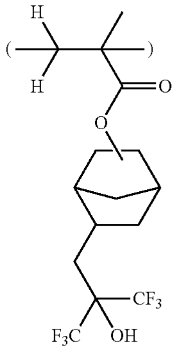

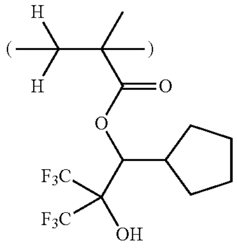

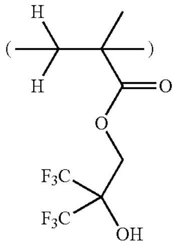

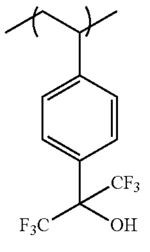

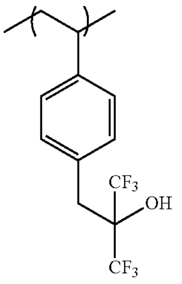

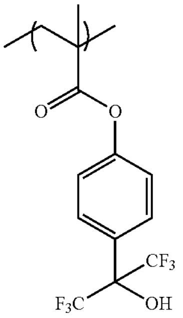

-continued

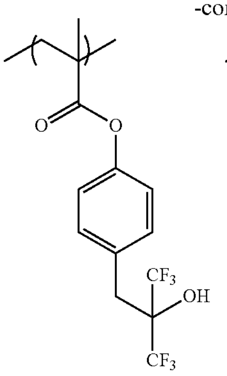

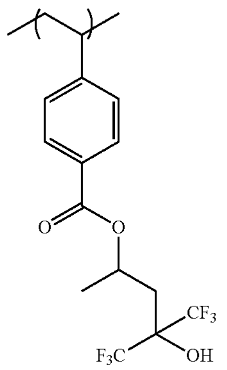

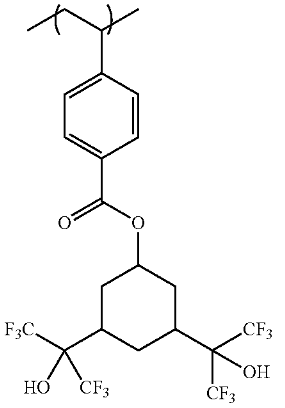

The polymer compound according to the invention preferably further contains one or more of a repeating unit shown by the following general formula (4) and a repeating unit shown by the following general formula (5). The repeating units shown by the general formula (4) and the general formula (5) are derived from cyclic olefins containing an aromatic ring.

(4)

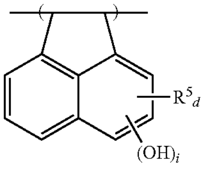

(5)

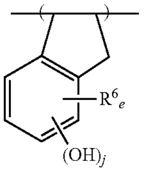

wherein $R^5$ and $R^6$ independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; "i" and "j" represent an integer of 0 to 3; "d" represents an integer of 0 to 5; and "e" represents an integer of 0 to 3.

A resist film obtained from a negative resist composition using the polymer compound that contains the repeating unit shown by the general formula (1), one or more of the repeating unit shown by the general formula (2) and the repeating unit shown by the general formula (3), and one or more of the repeating unit shown by the general formula (4) and the repeating unit shown by the general formula (5) together, can significantly inhibit pattern dependence on dimension of an irradiated pattern and a pattern to be formed even when a pattern exposure including both an isolated pattern and an isolated space pattern is performed with electron beam or EUV, as well as the resist film can have high resolution.

In the general formulae (4) and (5), $R^5$ and "d" and $R^6$ and "e" have the same meanings as $R^2$ and "a" in the general formula (1). Preferable examples thereof are also the same as them.

When repeating units in which "i" and "j" are 1 or more are used to improve alkali-solubility of the polymer compound in consideration of relation to the other repeating units constituting the polymer compound, the following available derivatives are preferably used to achieve the objective effect.

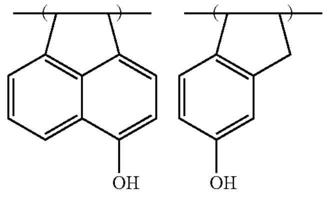

In this case, at least one repeating unit other than the repeating unit of formula (1) of the all repeating units constituting the inventive polymer compound preferably has a phenolic hydroxyl group unit and/or a fluoroalcohol group unit. The total amount of the repeating units other than the repeating unit of formula (1) is preferably 25 to 95 mol %, more preferably 40 to 90 mol %.

The polymer compound according to the invention preferably further contains one or more of a repeating unit shown by the following general formula (a1), a repeating unit shown by the following general formula (a2), and a repeating unit shown by the following general formula (a3), (a1)

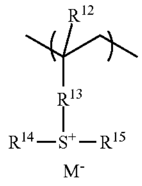

(a2)

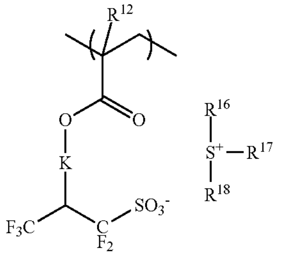

-continued (a3)

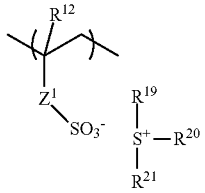

wherein $R^{12}$ independently represents a hydrogen atom or a methyl group; $R^{13}$ represents a single bond, a phenylene group, —O—$R^{22}$—, or —C(═O)—$Z^2$—$R^{22}$—, where $Z^2$ represents an oxygen atom or NH, and $R^{22}$ represents a phenylene group or a linear, branched, or cyclic alkylene group or alkenylene group having 1 to 6 carbon atoms and optionally containing a carbonyl group, an ester group, an ether group, or a hydroxyl group; K represents a single bond or —$Z^3$—C(═O)—O—, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, —O—$R^{23}$—, or —C(═O)—$Z^4$—$R^{23}$—, where $Z^4$ represents an oxygen atom or NH, and $R^{23}$ represents a phenylene group or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

As described above, $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom. A part of hydrogen atoms of these groups may be substituted with a heteroatom such as an oxygen atom, a sulfur atom, a nitrogen atom, and a halogen atom, or may contain a heteroatom such as an oxygen atom, a sulfur atom, and a nitrogen atom so as to form or contain a hydroxyl group, a cyano group, a carbonyl group, an ether bond, an ester bond, a sulfonate ester bond, a carbonate bond, a lactone ring, a sultone ring, a carboxylic anhydride, a haloalkyl group or the like.

When K in the general formula (a2) is —$Z^3$—C(═O)—O—, examples of the linear, branched, or cyclic divalent hydrocarbon group having 1 to 20 carbon atoms and optionally substituted with a heteroatom, represented by $Z^3$, include the following groups, although not limited thereto.

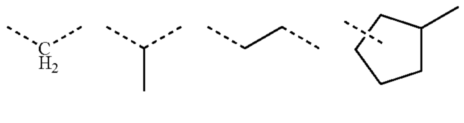

-continued

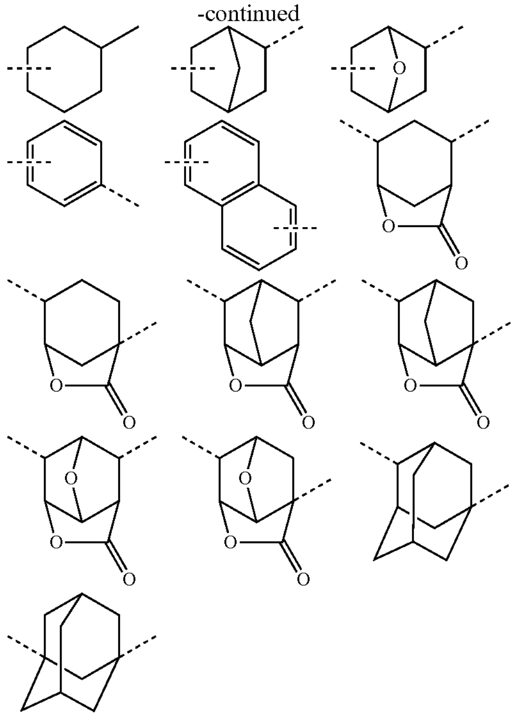

wherein the dotted line represents a bonding arm.

In the general formulae (a1) to (a3), $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula. Examples of this case include the following groups.

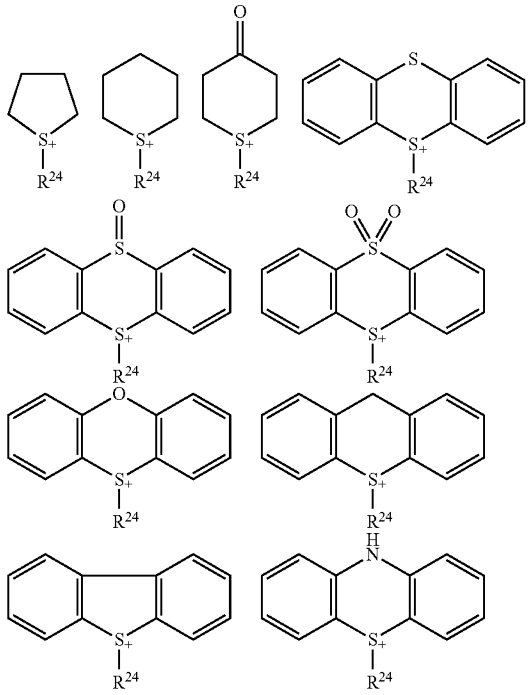

wherein $R^{24}$ represents the same group as $R^{13}$, $R^{16}$, $R^{17}$, $R^{18}$, $R^{19}$, $R^{20}$, and $R^{21}$.

Illustrative examples of the structure of the sulfonium cation shown by the general formulae (a2) and (a3) are shown below, although the present invention is not limited thereto.

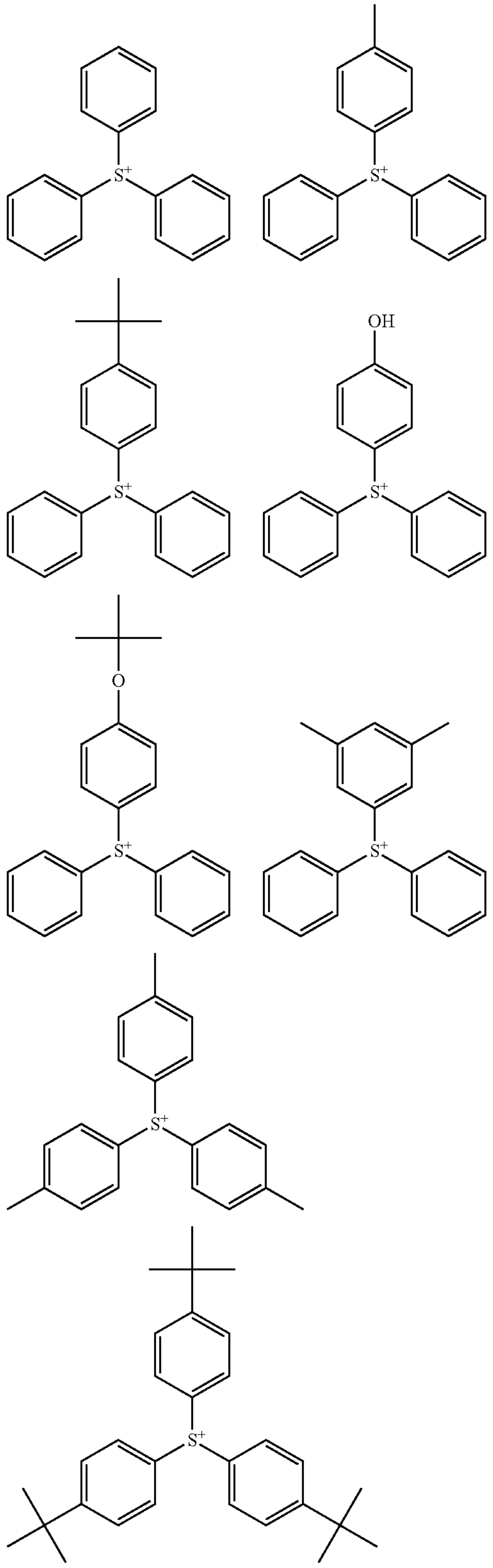

-continued
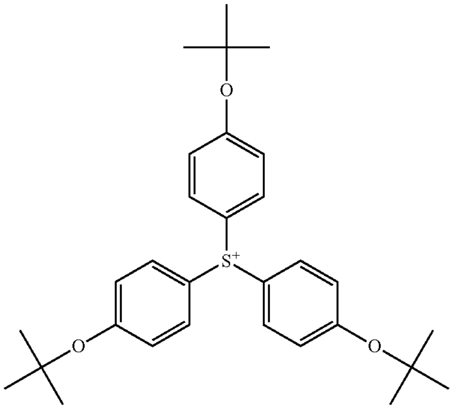
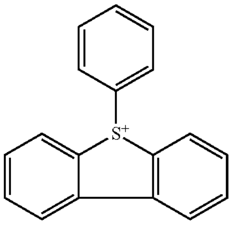
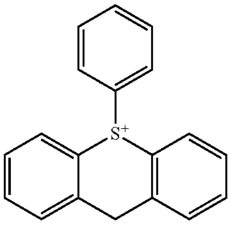
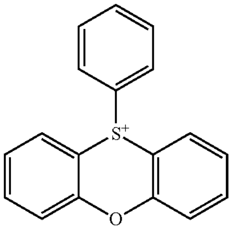
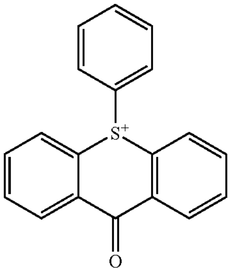
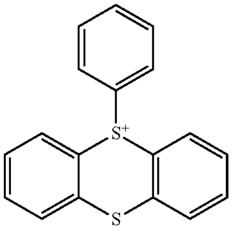
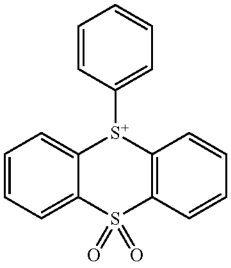
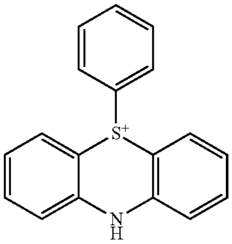
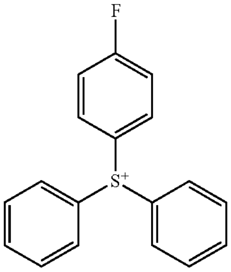
-continued
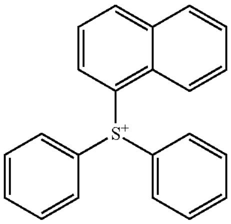
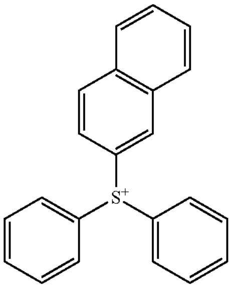
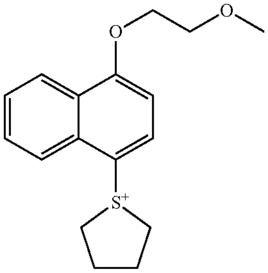
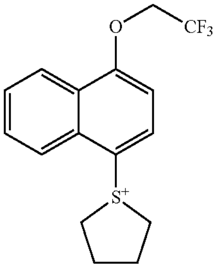
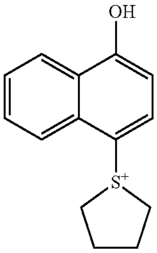
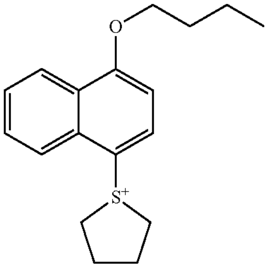
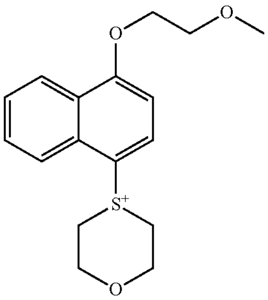
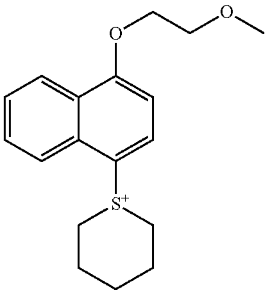

-continued

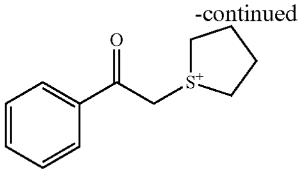

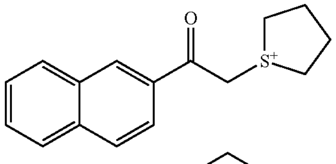

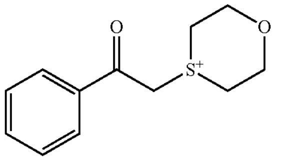

The repeating units shown by the general formulae (a1) to (a3) are repeating units that generate acid by irradiation with a high energy beam. When such repeating units are incorporated in the polymer compound, acid diffusion is appropriately controlled, and a pattern with a reduced LER can be obtained. Moreover, the polymer compound incorporating the acid generator units can inhibit a chemical flare phenomenon, where acid is vaporized from an exposed part and reattached to an unexposed part, at baking under vacuum, thus reducing LER and defects due to unexpected inhibition of the negative reaction at the unexposed part.

The inventive polymer compound is soluble in an aqueous alkaline developer. The group consisting of the repeating unit of formula (2) in which g≥1, the repeating unit of formula (3), the repeating unit of formula (4) in which i≥1, and the repeating unit of formula (5) in which j≥1 is a group of repeating units that provide alkali-solubility and substrate adhesion. Thus, the total amount of the repeating units of this group is preferably 25 to 95 mol %, more preferably 40 to 80 mol % with respect to all the repeating units constituting the polymer compound. In case that the total amount of the repeating unit of formula (4) in which i≥1 and the repeating unit of formula (5) in which j≥1 accounts for half or more of the repeating units of this group, the lower limit of the total amount of the group is preferably 40 mol %. Moreover, in case that the total amount of the repeating unit of formula (2) in which g≥1 and the repeating unit of formula (3) is 20 mol % or more of all the repeating units constituting the polymer compound, the upper limit of the total amount of the group is preferably 80 mol % or less. When the amount of the repeating units in the group is the above lower limit or more, scum is difficult to occur at development, and bridge is difficult to be formed in the resist pattern. In particular, when the repeating unit of formula (2) in which g≥1 is contained in an amount of 50 to 70 mol %, high resolution can be easily obtained.

A negative resist composition using the inventive polymer compound is made negative by inducing crosslinking of the polymer compound with a benzyl cation produced as a result of the elimination reaction by acid. To achieve this effect, the repeating unit shown by the general formula (1) is preferably contained in an amount of 1 to 75 mol %, more preferably 10 to 60 mol %, with respect to all the repeating units constituting the polymer compound. When the amount of the repeating unit shown by the general formula (1) is 5 mol % or more, alkali-solubility of the repeating unit shown by the general formula (1) is sufficiently changed by the reaction by acid, and the effect of the invention can be surely achieved.

To achieve tolerance to thermal vibration of the polymer compound, the total amount of the repeating unit shown by the general formula (4) and the repeating unit shown by the general formula (5) is preferably 3 to 30 mol %, more preferably 5 to 20 mol %, with respect to all the repeating units constituting the polymer compound.

The repeating units shown by the general formulae (a1) to (a3), which can generate acid by photo-exposure, are preferably contained in an amount of 0.5 to 20 mol %, more preferably 1 to 10 mol %. When the amount of the repeating units shown by the general formulae (a1) to (a3) is 20 mol % or less, the solubility of the polymer compound in a resist solvent can be prevented from decreasing, and there is no fear of defect occurrence.

Examples of other repeating units that can be contained include repeating units shown by the following general formulae (9) to (11). These repeating units are not acidic and can be optionally used as repeating units for imparting substrate adhesion or adjusting solubility.

(9)

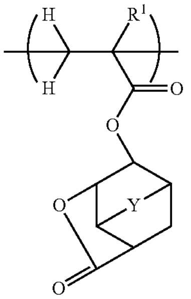

(10)

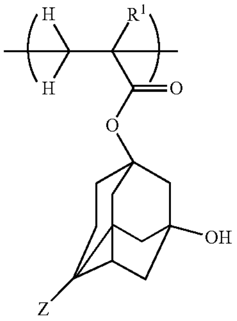

(11)

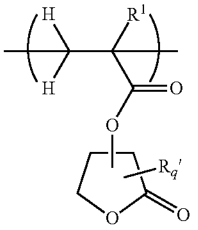

wherein $R^1$ is as defined above; Y represents an oxygen atom or a methylene group; Z represents a hydrogen atom or a hydroxyl group; R' represents an alkyl group having 1 to 4 carbon atoms; and "q" represents an integer of 0 to 3.

[Negative Resist Composition]

The present invention provides a negative resist composition containing the above-mentioned polymer compound.

The negative resist composition according to the invention may further contain a compound (an acid generator)

capable of generating acid by irradiation with a high energy beam. The adding amount thereof is preferably 1 to 20 parts by mass, more preferably 2 to 15 parts by mass, based on 100 parts by mass of the polymer compound. The acid generator is appropriately selected from known acid generators according to physical properties to be adjusted. Preferable examples of the acid generator include sulfonium salt, iodonium salt, sulfonyldiazomethane, N-sulfonyloxyimide, and oxime-o-sulfonate type acid generators. These acid generators may be used alone or in combination of two or more kinds.

Illustrative examples of the acid generator include materials disclosed in paragraphs (0122) to (0142) of Japanese Patent Laid-Open Publication No. 2008-111103.

Among the illustrative examples of the acid generator, arylsulfonate type photo acid generators, which can generate acid having an appropriate acidity to produce a benzyl cation from the repeating unit shown by the general formula (1) and induce the crosslinking reaction, are preferable.

As such an acid generator, compounds having the following sulfonium anion structure can be suitably used. As a counter cation, sulfonium cation disclosed in paragraph (0082) of the present description can be suitably used.

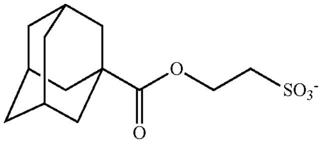
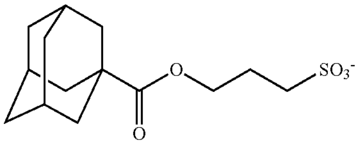
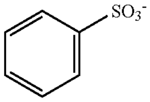
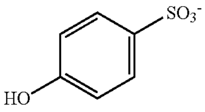
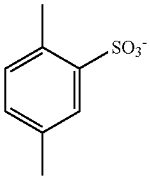
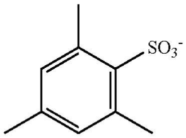
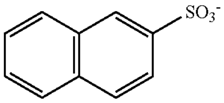
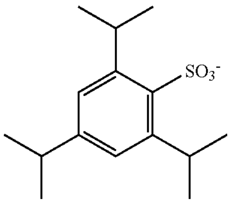
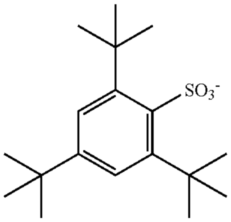
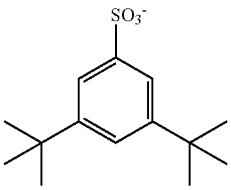
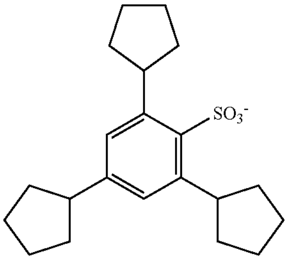

-continued

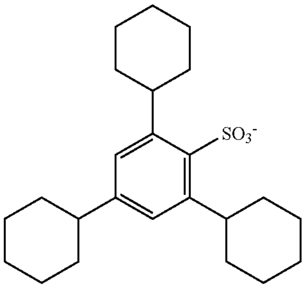
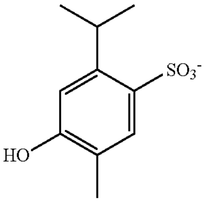
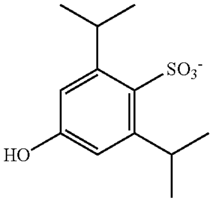
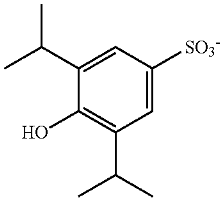
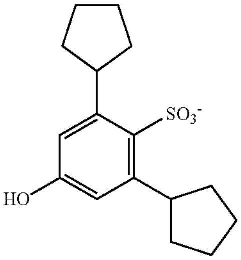
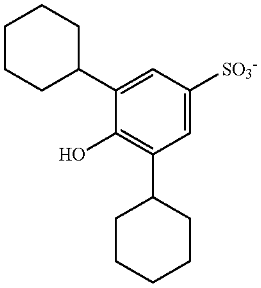
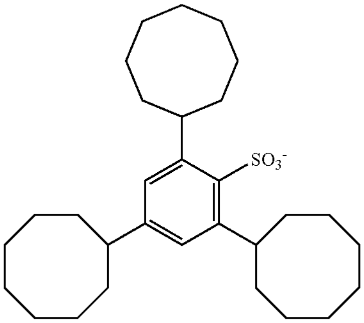

-continued
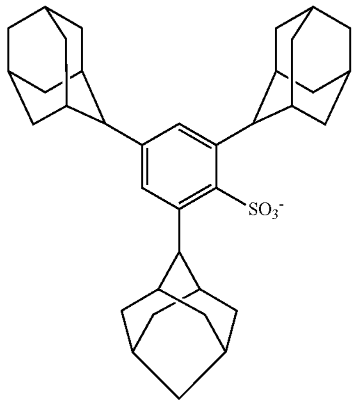
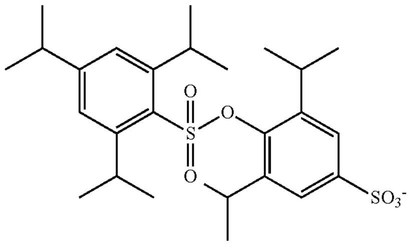
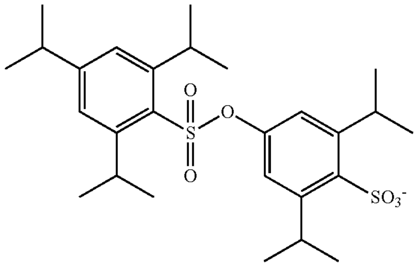
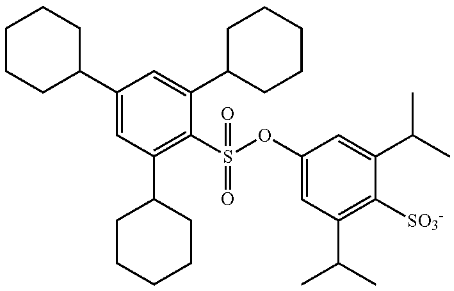
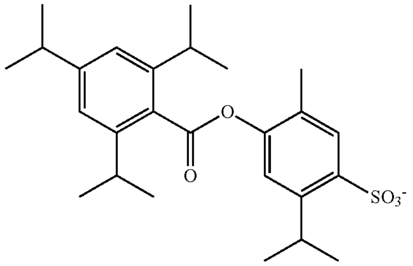
-continued
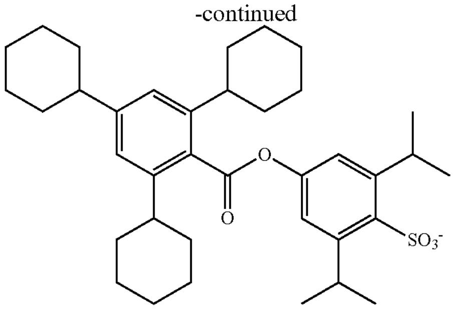
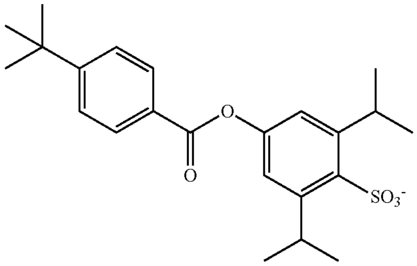
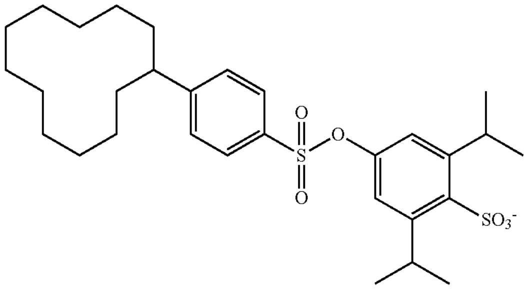
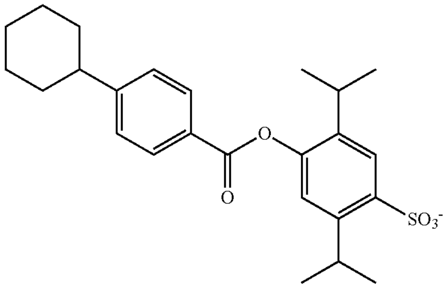
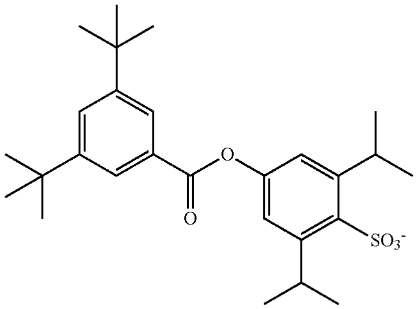
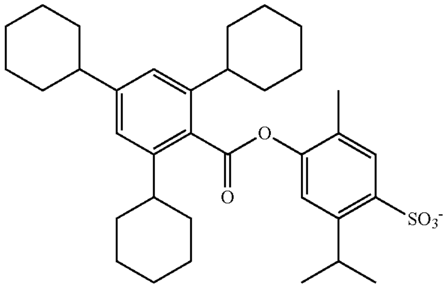

-continued
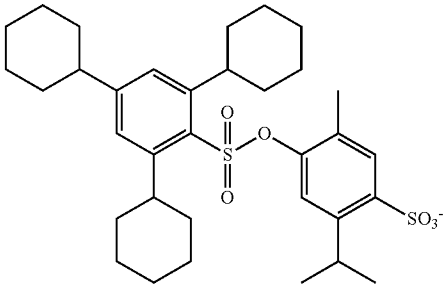
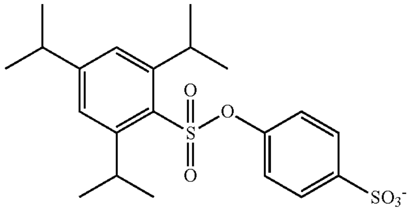
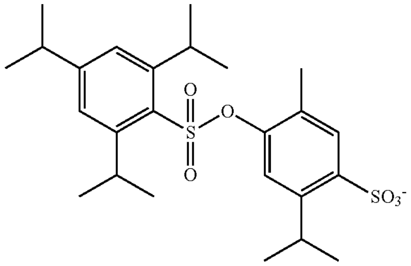
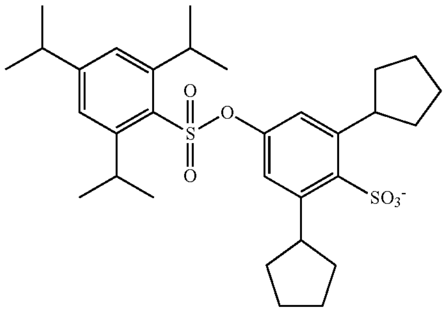
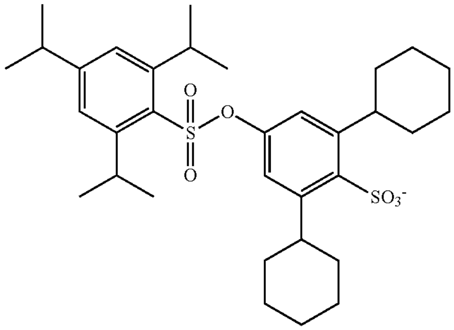
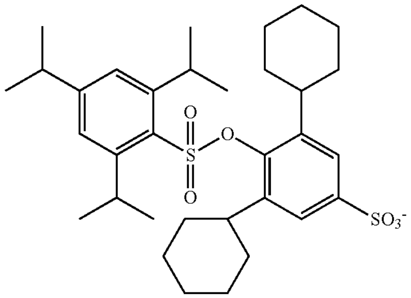
-continued
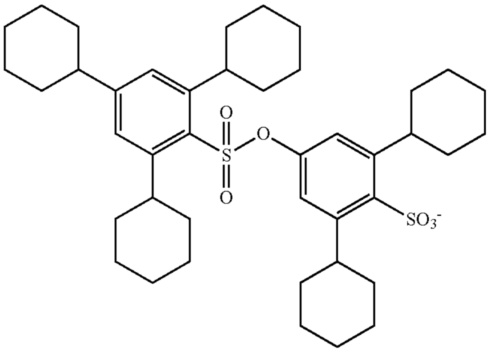
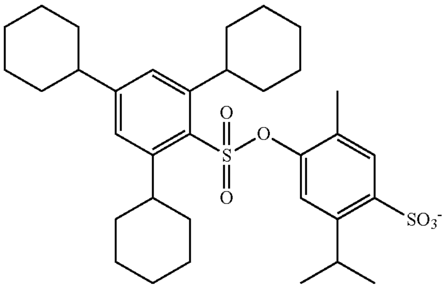
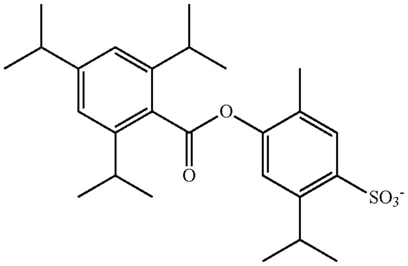
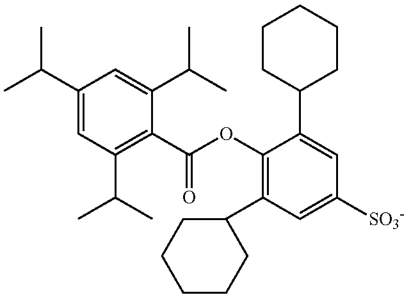
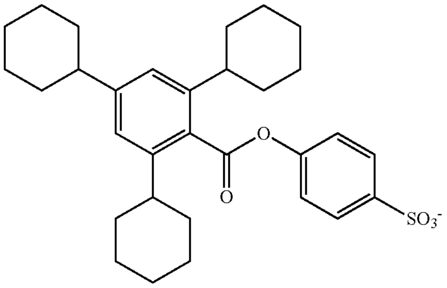

-continued
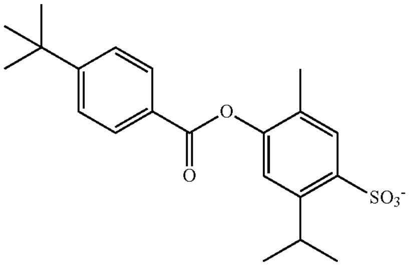
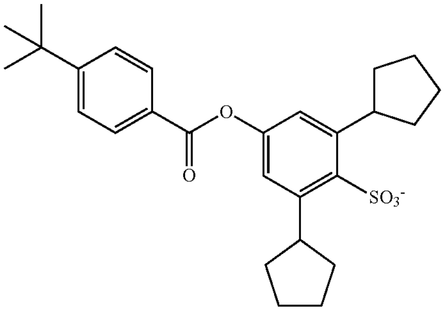
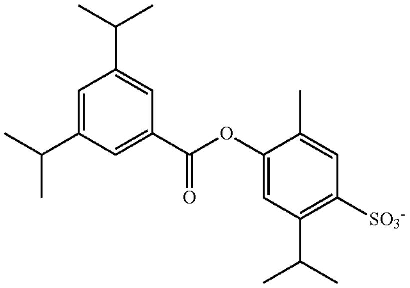
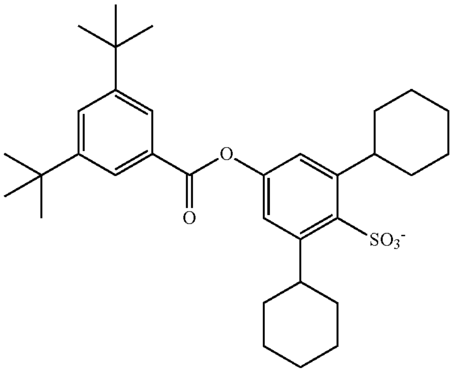
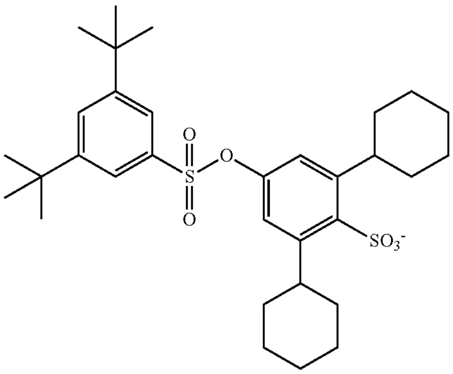
-continued
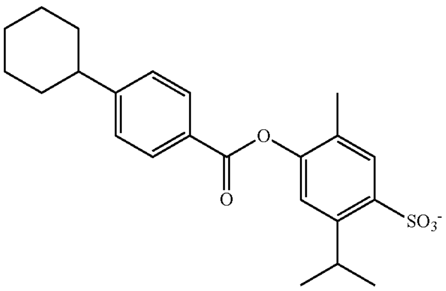
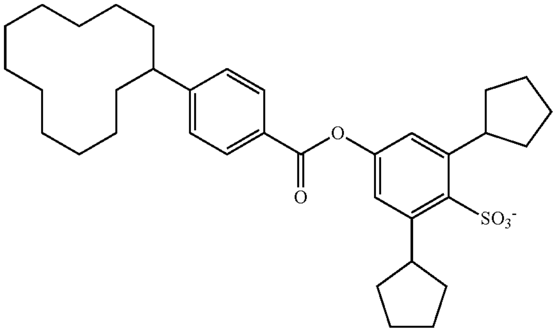
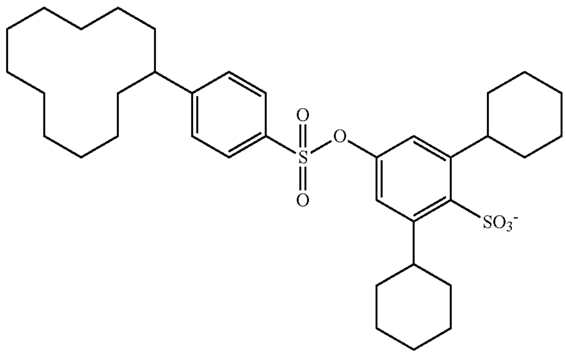
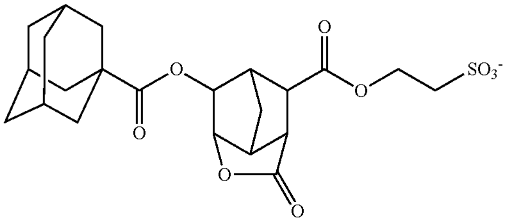
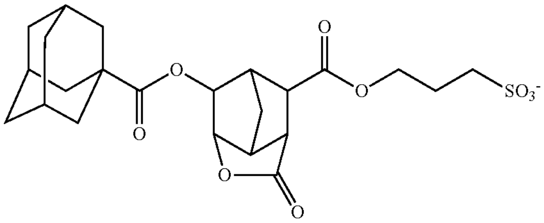
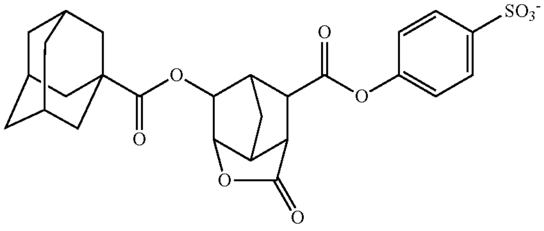

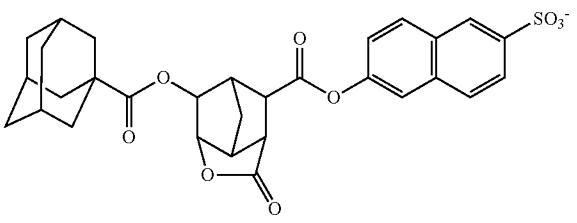
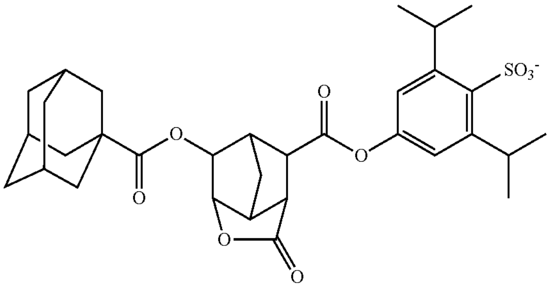
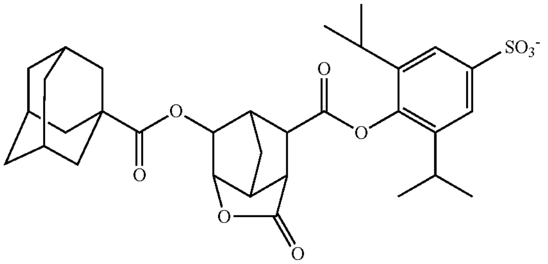
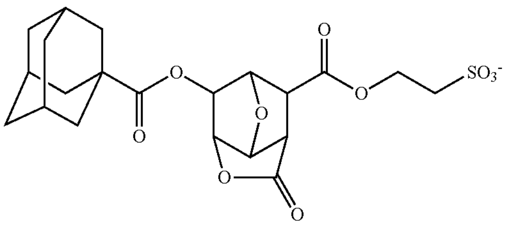
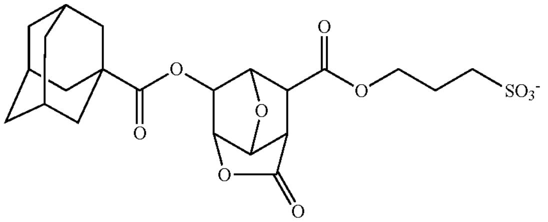
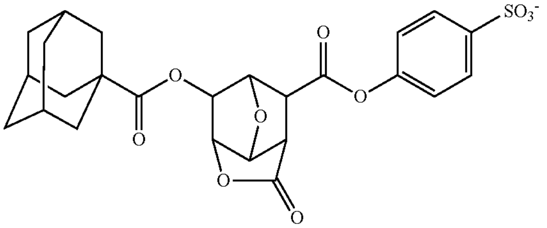
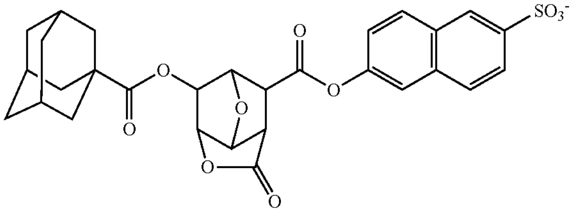
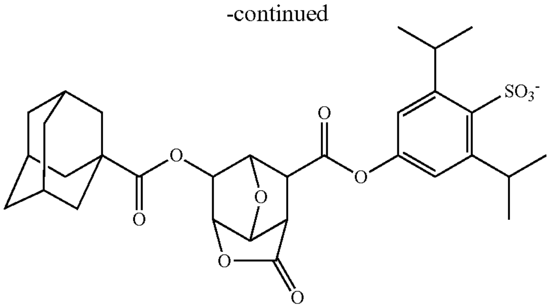
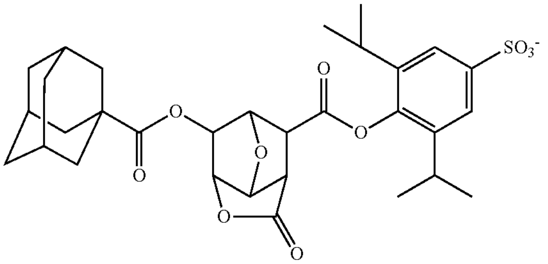
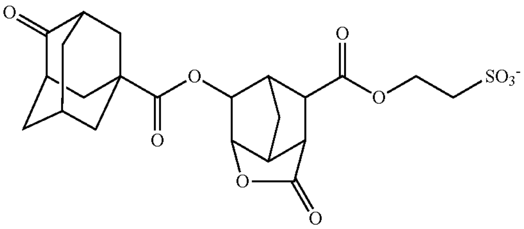
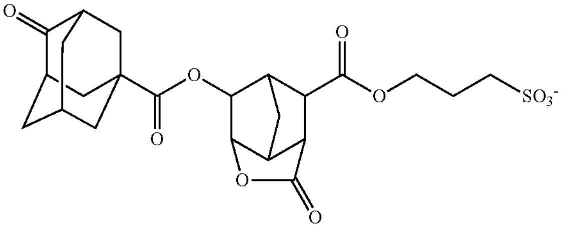
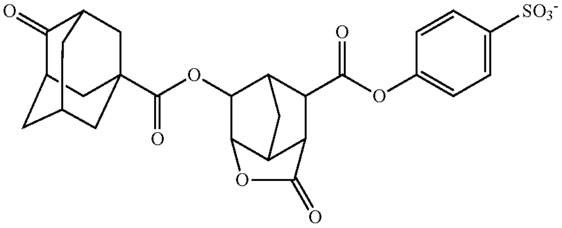
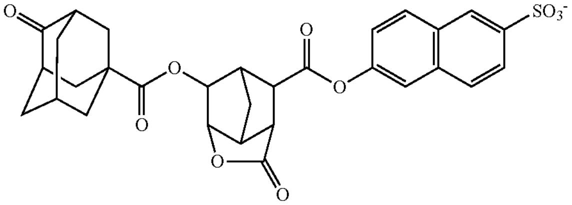
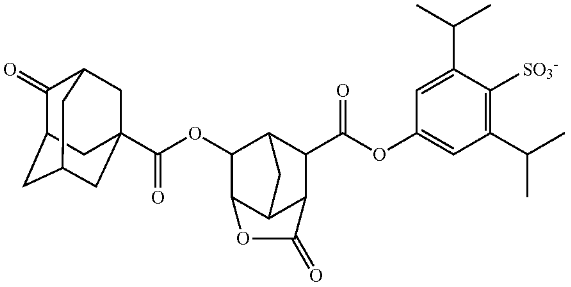

-continued

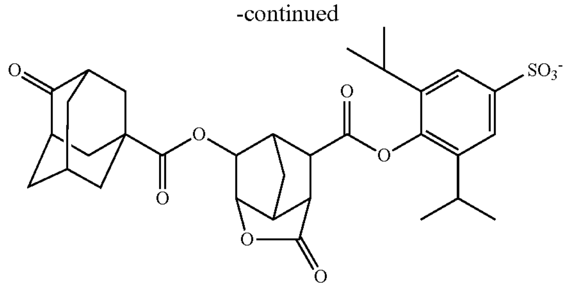

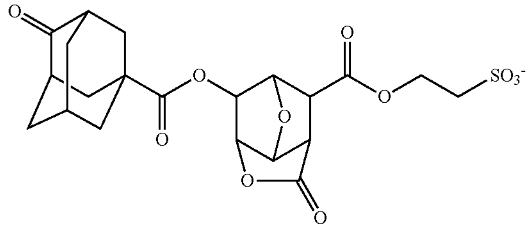

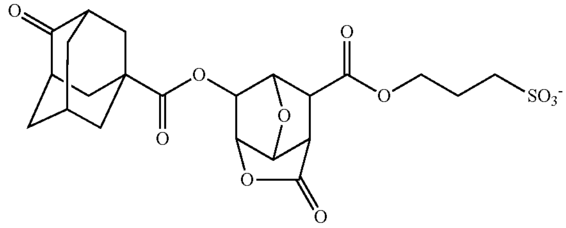

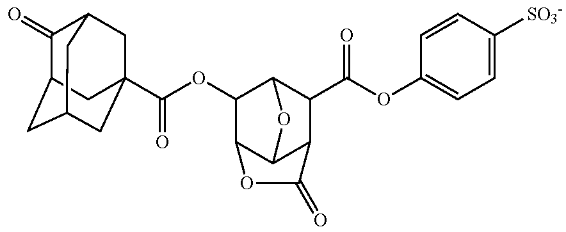

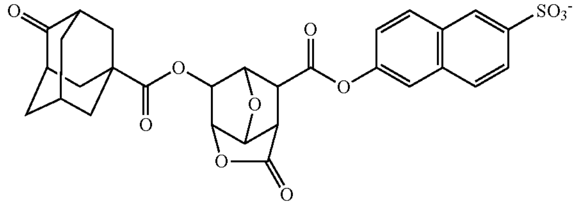

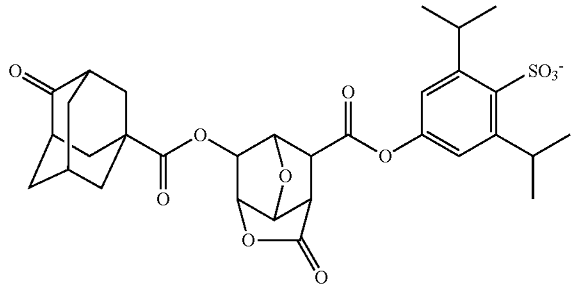

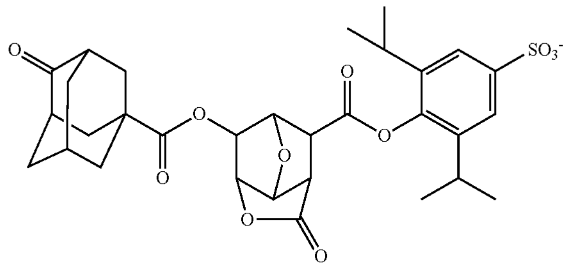

The inventive negative resist composition preferably contains an acid diffusion controlling agent to adjust sensitivity and achieve high resolution. The amount thereof is preferably 0.01 to 20 parts by mass, particularly preferably 0.05 to 15 parts by mass, based on 100 parts by mass of the polymer compound. As a basic compound to be blended, primary, secondary, and tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, nitrogen-containing alcoholic compounds, amides, imides, carbamates, ammonium salts, and carboxylates are known. Many examples thereof are disclosed in paragraphs (0146) to (0164) of Japanese Patent Laid-Open Publication No. 2008-111103 and Japanese Patent No. 3790649. In general, all compounds disclosed therein can be used, and two or more basic compounds may be selected to use the mixture.

Among the acid diffusion controlling agents, a salt shown by the following general formula (3a) is particularly preferably used.

$$R^{11}—CO_2^-Q^+ \quad (3a)$$

wherein $R^{11}$ represents a linear, branched, or cyclic alkyl group having 1 to 20 carbon atoms, alkenyl group having 2 to 20 carbon atoms, aryl group having 6 to 36 carbon atoms, in which these groups optionally contain a fluorine atom, a nitrogen atom, an ether group, an ester group, a lactone ring, a lactam ring, a carbonyl group, or a hydroxyl group; Q represents a counter cation having a substituent selected from a sulfonium cation, an iodonium cation, and an ammonium cation.

The salt shown by the general formula (3a) causes exchange reaction with acid generated by exposure, and thus functions as the acid diffusion controlling agent. This salt is an ionic compound and is not vaporized by heat. Meanwhile, an amine compound conventionally used as the acid diffusion controlling agent can be vaporized by heat caused at baking or drawing. The resist composition using the ionic compound as the acid diffusion controlling agent is not affected by heat caused at baking or drawing and has an advantage of low temperature dependence on the pattern dimension.

Illustrative examples of the anion structure of the salt shown by the general formula (3a) are shown below, but the present invention is not limited thereto.

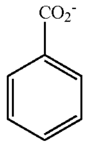
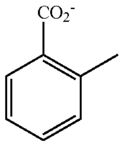
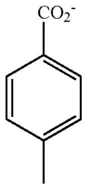
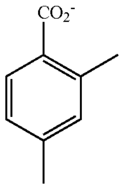

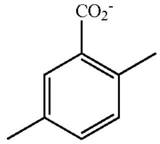
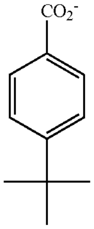
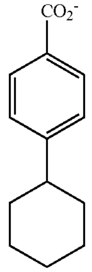

-continued
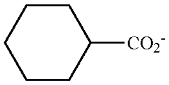
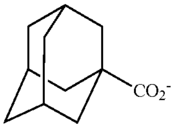
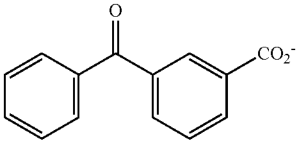
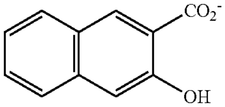
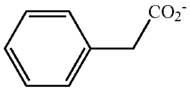
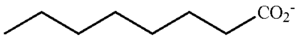
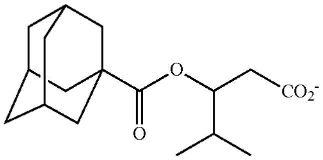
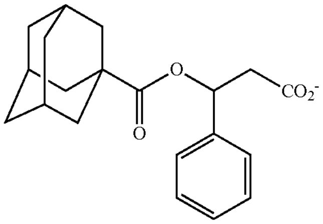
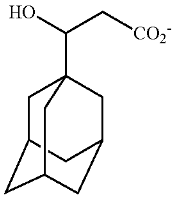
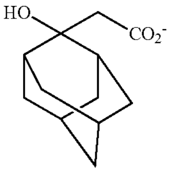
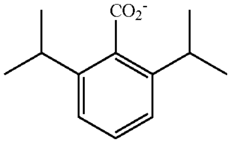
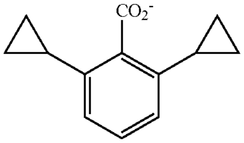
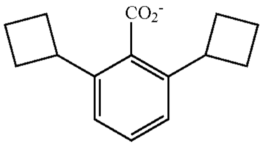
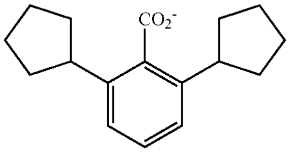
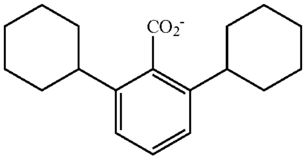
-continued
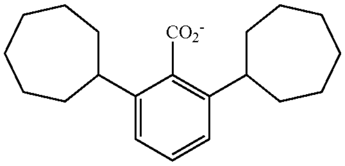
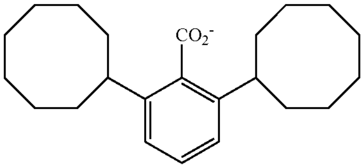
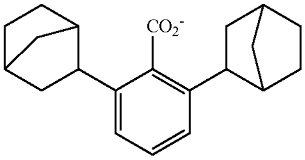
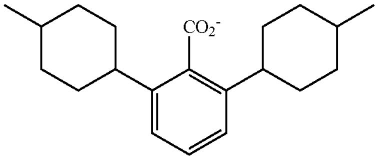
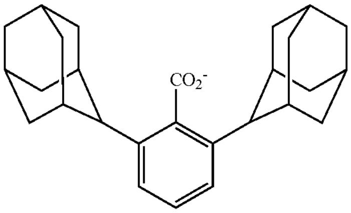
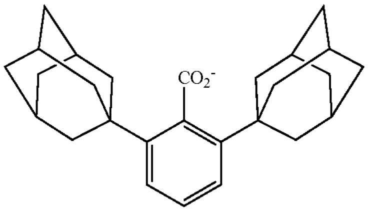
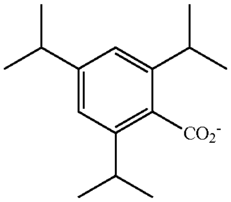
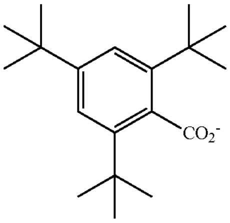
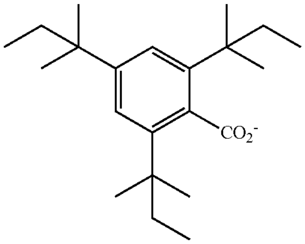

-continued

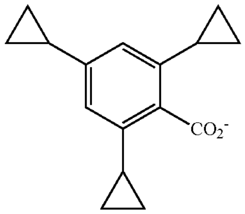

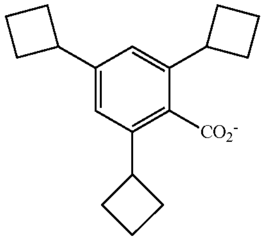

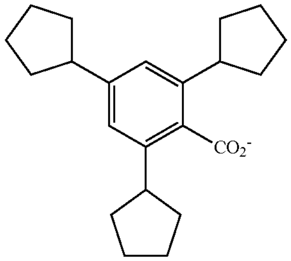

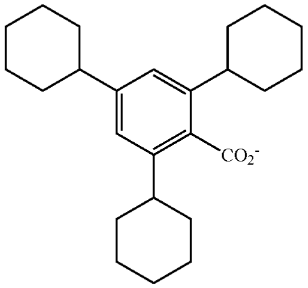

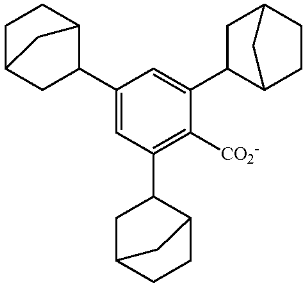

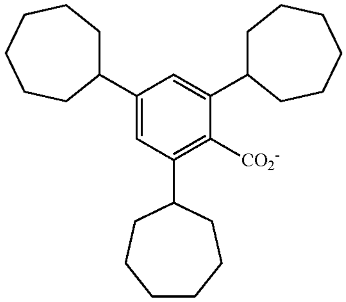

-continued

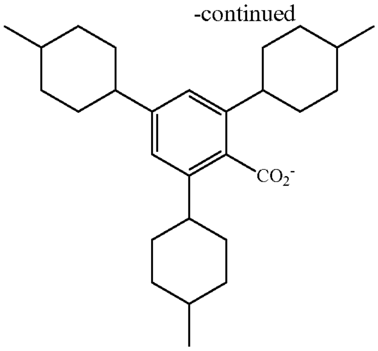

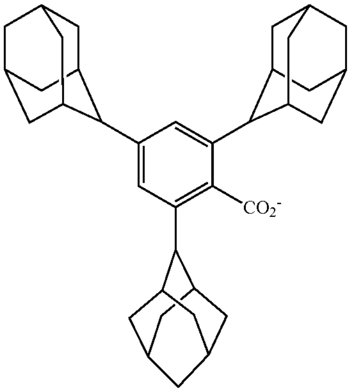

A crosslinking agent is not basically added to the inventive negative resist composition, but if the properties require finely adjusting, a crosslinking agent may be added in an amount of about 0.5 to 5 parts by mass based on 100 parts by mass of the polymer compound. Many crosslinking agent are known for negative resist compositions, as disclosed in Patent Documents 1 to 3.

This additional crosslinking agent is preferably alkoxymethylglycoluril or alkoxymethyl melamine. Illustrative examples thereof include tetramethoxymethylglycoluril, 1,3-bismethoxymethyl-4,5-bismethoxyethylene urea, bismethoxymethyl urea, hexamethoxymethyl melamine, and hexaethoxymethyl melamine. The crosslinking agent may be used alone or in combination of multiple kinds.

To the inventive negative resist composition may be added a surfactant conventionally used to improve coating property. The surfactant to be used may be selected from many known materials as disclosed in Patent Documents 1 to 5. In addition, a polymer containing fluorine as disclosed in Japanese Patent Laid-Open Publication No. 2008-304590 may be added.

The adding amount of the surfactant is preferably 2 parts by mass or less, more preferably 1 part by mass or less, based on 100 parts by mass of the whole polymer compound in the negative resist composition. When the surfactant is added, the amount is preferably 0.01 part by mass or more.

The organic solvent to be used for preparing the inventive negative resist composition may be any organic solvent that can dissolve the polymer compound, the acid generator, and other additives. Examples of the organic solvent include ketones such as cyclohexanone and methyl-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combination of two or more kinds, although it is not limited thereto. Among these organic solvents, ethyl lactate, propylene glycol monomethyl ether, propylene glycol monomethyl ether acetate, and a mixed solvent thereof, which are most excellent in solubility of an acid generator in the resist composition, are preferably used in the present invention.

The amount of the organic solvent to be used is preferably 1,000 to 10,000 parts by mass, particularly preferably 2,000 to 9,700 parts by mass, based on 100 parts by mass of the whole polymer compound. When the concentration is adjusted in this range, a resist film 10 to 300 nm thick can be stably formed with high flatness by spin coating.

Furthermore, known surfactants and dissolution inhibitors may be appropriately added to the inventive negative resist composition.

[Laminate]

Furthermore, the present invention provides a laminate containing a resist film formed from the above-mentioned negative resist composition on a photomask blank.

(Patterning Process)

The present invention provides a patterning process including the steps of: forming a resist film from the above-mentioned negative resist composition on a substrate to be processed; pattern-irradiating the resist film with a high energy beam; and developing the resist film with an alkaline developer to form a resist pattern.

To form a pattern using the inventive negative resist composition, a known lithography technology may be employed. In general, the composition is applied onto a substrate to be processed, for example, a substrate for manufacturing integrated circuits, such as a silicon wafer having a surface layer of Si, $SiO_2$, SiN, SiON, TiN, WSi, BPSG, SOG, or an organic antireflection film, or a substrate (photomask blank) for manufacturing mask circuits, such as a quartz substrate having a surface layer of Cr, CrO, CrON, or MoSi, by a method such as spin coating so as to give a film thickness of 0.05 to 2.0 m and then pre-baked on a hot plate at 60 to 150° C. for 1 to 10 minutes, preferably at 80 to 140° C. for 1 to 5 minutes. In particular, a photomask blank having an outermost surface formed of a chromium material is preferably used.

Then, the film is exposed to a high energy beam such as far ultraviolet ray, excimer laser beam, X-ray, EUV, or electron beam through a mask for forming an intended pattern or by beam exposure, with an exposure dose of 1 to 200 $mJ/cm^2$, preferably 10 to 100 $mJ/cm^2$. The exposure may be performed by a usual exposure method or, if necessary, an immersion method in which a liquid is placed between the mask and the resist film. In this case, a top coat that is insoluble in water can be used.

Subsequently, post-exposure bake (PEB) is carried out on a hot plate at 60 to 150° C. for 1 to 10 minutes, preferably at 80 to 140° C. for 1 to 5 minutes. Thereafter, the film is then developed by a usual method such as dip method, puddle method, or spray method, with a developer of an alkaline aqueous solution such as 0.1 to 5 mass %, preferably 2 to 3 mass % tetramethylammonium hydroxide (TMAH) solution, for 0.1 to 3 minutes, preferably 0.5 to 2 minutes. The intended pattern can be thus formed on the substrate.

The inventive negative resist composition has especially high etching resistance. Thus, this composition can withstand severe etching conditions and can be suitably used under conditions that require small LER. In addition, this composition is particularly useful for a substrate (a substrate to be processed) coated with a material that is difficult to adhere to the resist pattern and easily causes pattern peeling and pattern collapse, and is useful for patterning on a substrate, especially on a photomask blank, having a film formed by sputtering metal chromium or a chromium compound containing one or more light elements such as oxygen, nitrogen, and carbon.

EXAMPLES

Hereinafter, the present invention will be specifically described with reference to Synthesis Examples, Comparative Synthesis Examples, Examples, and Comparative Examples, but the present invention is not limited the following examples. In the following, copolymerization composition ratio means mole ratio, and weight average molecular weight (Mw) means a weight average molecular weight measured by gel permeation chromatography (GPC) in terms of polystyrene.

[Synthesis Example 1] Synthesis of Monomer

Synthesis of 4-(1-hydroxy-2,2-dimethyl-1-propyl)styrene

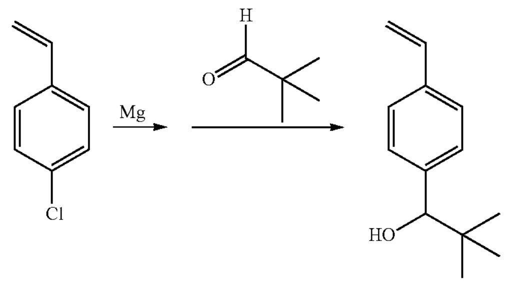

Under a nitrogen atmosphere, a 3-L four-necked flask was charged with 31.1 g of magnesium and 50 mL of THF, and a solution in which 177 g of chlorostyrene has been dissolved in 300 mL of THF was added dropwise thereto at room temperature over 1 hour. The mixture was heated to 40° C. and then stirred for 3 hours to prepare a Grignard reagent. The obtained Grignard reagent was cooled in an ice-bath, and a solution in which 79.3 g of pivalaldehyde has been dissolved in 200 mL of THF was added dropwise thereto over 1 hour. After stirring overnight, 15 mass % ammonium chloride aqueous solution (1,000 g) was added dropwise to terminate the reaction. The product was then subjected to a usual aqueous post-treatment (aqueous work-up) and purified by distillation to obtain 184 g of the intended compound, 4-(l-hydroxy-2,2-dimethyl-1-propyl) styrene (yield: 76%). This compound satisfies the general formula (1a).

IR and $^1H$-NMR measurement results of the obtained compound are shown below.

IR(D-ATR): ν=3442, 2953, 2905, 2868, 1630, 1511, 1479, 1464, 1406, 1393, 1363, 1290, 1234, 1208, 1176, 1050, 1005, 989, 905, 849, 834, 776 $cm^{-1}$ $^1H$-NMR (600 MHz in DMSO-d6): δ=7.38 (2H, d), 7.24 (2H, d), 6.70 (1H, dd), 5.78 (1H, d), 5.20 (1H, d), 4.21 (1H, d), 0.82 (9H, d) ppm

[Synthesis Example 2] Synthesis of Polymer Compound (Polymer)

Polymer compounds (polymers) used for preparing negative resist compositions were synthesized in the following manner.

[Synthesis Example 2-1] Synthesis of Polymer 1

Under a nitrogen atmosphere, a 500-mL dropping cylinder was charged with 117 g of a PGMEA solution containing 50.0 wt % 4-hydroxystyrene, 4.99 g of acenaphthylene, 23.4 g of 4-(1-hydroxy-1-phenylmethyl)styrene, 12.9 g of triphenylsulfonium-1,1,3,3,3-pentafluoro-2-methacryloyloxy-propane-1-sulfonate, 12.1 g of dimethyl-2,2'-azobis-(2-methylpropionate) (Product name: V-601, available from Wako Pure Chemical Industries, Ltd.), and as solvents, 67 g of γ-butyrolactone and 26 g of PGMEA to prepare a solution. Further, another 1000-mL flask for polymerization under a nitrogen atmosphere was charged with 78 g of γ-butyrolactone, and the above-prepared solution was added dropwise thereto over 4 hours under heating at 80° C. After completion of dropwise addition, the solution was stirred for 18 hours while the polymerization temperature was maintained at 80° C., followed by cooling to room temperature. The obtained polymerization solution was added dropwise to 3,000 g of diisopropyl ether to agglomerate a copolymer. The diisopropyl ether was removed by decantation, and the copolymer was dissolved in 200 g of acetone. This acetone solution was added dropwise to 3,000 g of diisopropyl ether, and the precipitated copolymer was collected by filtration. The collected copolymer was again dissolved in 200 g of acetone. This acetone solution was added dropwise to 3,000 g of water, and the precipitated copolymer was collected by filtration. Thereafter, the copolymer was dried at 40° C. for 40 hours to obtain 72 g of a white polymer. The obtained polymer was measured by $^{13}$C-NMR, $^{1}$H-NMR, and GPC, providing the following analytical results.

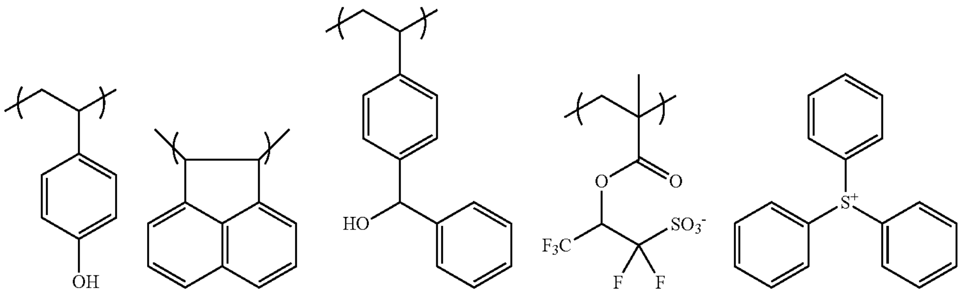

| Copolymerization composition ratio | 74.5 | 5 | 17 | 3.5 |
|---|---|---|---|---|

Weight average molecular weight (Mw)=13,500

Molecular weight distribution (Mw/Mn)=1.64

This polymer is named Polymer 1.

[Synthesis Examples 2-2 to 2-14] Synthesis of Polymers 2 to 14

Polymers 2 to 14 shown in Table 1 were synthesized in the same manner as in Synthesis Example 2-1 except for changing the kind and the blending ratio of monomers. In Table 1, introducing ratio means mole ratio. Structures of repeating units introduced in the polymers are shown in Tables 4 to 7.

[Synthesis Example 2-15] Synthesis of Polymer 15

Under a nitrogen atmosphere, a 200-mL dropping cylinder was charged with 36.6 g of 4-acetoxystyrene, 3.60 g of acenaphthylene, 9.95 g of 4-(l-hydroxy-1-phenylmethyl) styrene, 5.45 g of dimethyl-2,2'-azobis-(2-methylpropionate) (Product name: V-601, available from Wako Pure Chemical Industries, Ltd.), and as a solvent, 56 g of methyl ethyl ketone to prepare a solution. Further, another 500-mL flask for polymerization under a nitrogen atmosphere was charged with 38 g of methyl ethyl ketone, and the above-prepared solution was added dropwise thereto over 4 hours under heating at 80° C. After completion of dropwise addition, the solution was stirred for 18 hours while the polymerization temperature was maintained at 80° C., followed by cooling to room temperature. The obtained polymerization solution was added dropwise to 700 g of hexane, and the precipitated copolymer was collected by filtration. The collected copolymer was washed with 140 g of hexane twice. The obtained copolymer was dissolved in a mixed solvent of 90 g of tetrahydrofuran and 30 g of methanol in a 1-L flask under a nitrogen atmosphere. The solution was mixed with 16.5 g of ethanolamine and stirred at 60° C. for 3 hours. The reaction solution was concentrated under reduced pressure, and the concentrated product was dissolved in a mixed solvent of 210 g of ethyl acetate and 80 g of water. The obtained solution was transferred to a separating funnel, and 8.2 g of acetic acid was added for liquid separation. A lower layer of the solution was distilled off, and 80 g of water and 10.9 g of pyridine were added to the obtained organic layer for liquid separation again. Further, the lower layer was distilled off, and 80 g of water was added to the obtained organic layer to perform water-washing liquid separation (five times). After the liquid separation, the organic layer was concentrated and then dissolved in 100 g of acetone. The obtained acetone solution was added dropwise to 1,500 g of water, and a crystallized deposit thus obtained was filtered and washed with water. After the resultant was subjected to suction-filtration for 2 hours, the filtered product was again dissolved in 150 g of acetone. The obtained acetone solution was added dropwise to 1,500 g of water, and a crystallized deposit thus obtained was filtered, washed with water, and dried to obtain 31.0 g of a white polymer. The obtained polymer was measured by $^{13}$C-NMR, $^{1}$H-NMR, and GPC, providing the following analytical results.

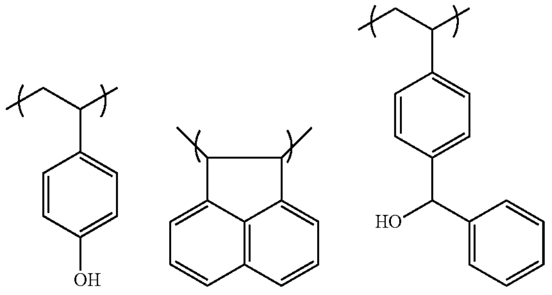

| Copolymerization composition ratio | 76 | 8 | 16 |
|---|---|---|---|

Weight average molecular weight (Mw)=3,800
Molecular weight distribution (Mw/Mn)=1.63
This polymer is named Polymer 15.

[Synthesis Example 2-16] Synthesis of Polymer 16

Under a nitrogen atmosphere, a 200-mL dropping cylinder was charged with 36.3 g of hydroquinone monomethacrylate, 3.35 g of acenaphthylene, 10.4 g of 4-(1-hydroxy-1-phenylmethyl)styrene, 5.06 g of dimethyl-2,2'-azobis-(2-methylpropionate) (Product name: V-601, available from Wako Pure Chemical Industries, Ltd.), and as a solvent, 56 g of methyl ethyl ketone to prepare a solution. Further, another 500-mL flask for polymerization under a nitrogen atmosphere was charged with 38 g of methyl ethyl ketone, and the above-prepared solution was added dropwise thereto over 4 hours under heating at 80° C. After completion of dropwise addition, the solution was stirred for 18 hours while the polymerization temperature was maintained at 80° C., followed by cooling to room temperature. The obtained polymerization solution was added dropwise to 1,000 g of hexane, and the precipitated copolymer was collected by filtration. The collected copolymer was washed with 200 g of hexane twice. The obtained copolymer was filtered and dried to obtain 45.0 g of a white polymer. The obtained polymer was measured by $^{13}$C-NMR, $^{1}$H-NMR, and GPC, providing the following analytical results.

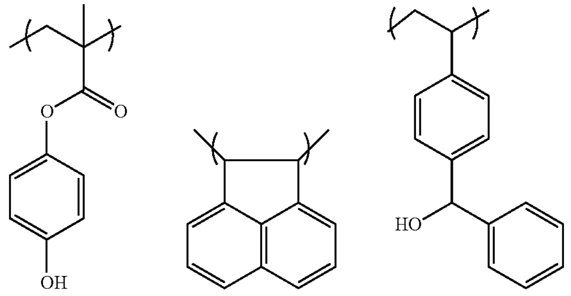

| Copolymerization composition ratio | 74 | 8 | 18 |
|---|---|---|---|

Weight average molecular weight (Mw)=4,400
Molecular weight distribution (Mw/Mn)=1.67
This polymer is named Polymer 16.

[Synthesis Examples 2-17 to 2-24] Synthesis of Polymers 17 to 24

Polymers 17 to 24 shown in Table 1 were synthesized in the case of polymers containing A-1 unit as in Synthesis Example 2-15, and in the case of polymers containing A-2 unit as in Synthesis Example 2-16, except for changing the kind and the blending ratio of monomers.

[Synthesis Examples 2-25 to 2-37] Synthesis of Polymers 25 to 37

Polymers 25 to 37 shown in Table 2 were synthesized in the same manner as in Synthesis Example 2-1 except for changing the kind and the blending ratio of monomers. In Table 2, introducing ratio means mole ratio.

[Synthesis Examples 2-38 to 2-46] Synthesis of Polymers 38 to 46

Polymers 38 to 46 shown in Table 2 were synthesized in the case of polymers containing A-1 unit as in Synthesis Example 2-15, and in the case of polymers containing A-2 unit as in Synthesis Example 2-16, except for changing the kind and the blending ratio of monomers.

[Comparative Synthesis Examples 1 to 4] Synthesis of Comparative Polymers 1 to 4

Comparative Polymers 1 to 4 shown in Table 3 were synthesized in the same manner as in Synthesis Example 2-1 except for changing the kind and the blending ratio of monomers. In Table 3, introducing ratio means mole ratio.

[Comparative Synthesis Examples 5 to 8] Synthesis of Comparative Polymers 5 to 8

Comparative Polymers 5 to 8 shown in Table 3 were synthesized in the same manner as in Synthesis Example 2-15 except for changing the kind and the blending ratio of monomers.

TABLE 1

| | Unit 1 | Introducing ratio (mol %) | Unit 2 | Introducing ratio (mol %) | Unit 3 | Introducing ratio (mol %) | Unit 4 | Introducing ratio (mol %) |
|---|---|---|---|---|---|---|---|---|
| Polymer 1 | A-1 | 74.5 | B-2 | 5.0 | C-1 | 17.0 | P-1 | 3.5 |
| Polymer 2 | A-2 | 72.5 | B-2 | 6.0 | C-1 | 18.0 | P-1 | 3.5 |
| Polymer 3 | A-1 | 72.5 | B-1 | 6.0 | C-1 | 18.0 | P-1 | 3.5 |
| Polymer 4 | A-2 | 71.5 | B-1 | 7.0 | C-1 | 18.0 | P-1 | 3.5 |
| Polymer 5 | A-1 | 73.5 | B-2 | 5.0 | C-1 | 18.0 | P-2 | 3.5 |
| Polymer 6 | A-1 | 74.5 | B-2 | 5.0 | C-1 | 17.0 | P-3 | 3.5 |
| Polymer 7 | A-1 | 74.5 | B-2 | 5.0 | C-1 | 17.0 | P-4 | 3.5 |
| Polymer 8 | A-1 | 75.5 | B-2 | 5.0 | C-1 | 16.0 | P-5 | 3.5 |
| Polymer 9 | A-1 | 74.5 | B-2 | 5.0 | C-1 | 17.0 | P-6 | 3.5 |
| Polymer 10 | A-1 | 72.5 | B-3 | 8.0 | C-1 | 16.0 | P-1 | 3.5 |
| Polymer 11 | A-2 | 73.5 | B-4 | 7.0 | C-1 | 16.0 | P-3 | 3.5 |
| Polymer 12 | A-1 | 75.5 | B-2 | 5.0 | C-2 | 16.0 | P-1 | 3.5 |
| Polymer 13 | A-1 | 76.5 | B-2 | 5.0 | C-3 | 15.0 | P-1 | 3.5 |
| Polymer 14 | A-1 | 79.5 | B-2 | 5.0 | C-4 | 12.0 | P-1 | 3.5 |
| Polymer 15 | A-1 | 76.0 | B-2 | 8.0 | C-1 | 16.0 | — | — |
| Polymer 16 | A-2 | 74.0 | B-2 | 8.0 | C-1 | 18.0 | — | — |
| Polymer 17 | A-1 | 72.0 | B-1 | 9.0 | C-1 | 19.0 | — | — |
| Polymer 18 | A-1 | 70.0 | B-3 | 13.0 | C-1 | 17.0 | — | — |
| Polymer 19 | A-1 | 71.0 | B-4 | 13.0 | C-1 | 16.0 | — | — |
| Polymer 20 | A-1 | 76.0 | B-2 | 8.0 | C-2 | 16.0 | — | — |
| Polymer 21 | A-1 | 78.0 | B-2 | 7.0 | C-3 | 15.0 | — | — |
| Polymer 22 | A-1 | 81.0 | B-2 | 7.0 | C-4 | 12.0 | — | — |
| Polymer 23 | A-2 | 73.0 | B-3 | 11.0 | C-1 | 16.0 | — | — |
| Polymer 24 | A-2 | 73.0 | B-4 | 11.0 | C-1 | 16.0 | — | — |

TABLE 2

| | Unit 1 | Introducing ratio (mol %) | Unit 2 | Introducing ratio (mol %) | Unit 3 | Introducing ratio (mol %) | Unit 4 | Introducing ratio (mol %) |
|---|---|---|---|---|---|---|---|---|
| Polymer 25 | A-1 | 70.5 | B-2 | 7.0 | C-6 | 19.0 | P-1 | 3.5 |
| Polymer 26 | A-2 | 68.5 | B-2 | 8.0 | C-6 | 20.0 | P-1 | 3.5 |
| Polymer 27 | A-1 | 72.5 | B-1 | 6.0 | C-6 | 18.0 | P-1 | 3.5 |
| Polymer 28 | A-2 | 72.5 | B-1 | 6.0 | C-6 | 18.0 | P-1 | 3.5 |
| Polymer 29 | A-1 | 73.5 | B-2 | 7.0 | C-6 | 16.0 | P-2 | 3.5 |
| Polymer 30 | A-1 | 72.5 | B-2 | 7.0 | C-6 | 17.0 | P-3 | 3.5 |
| Polymer 31 | A-1 | 73.5 | B-2 | 6.0 | C-6 | 17.0 | P-4 | 3.5 |
| Polymer 32 | A-1 | 71.5 | B-2 | 7.0 | C-6 | 18.0 | P-5 | 3.5 |
| Polymer 33 | A-1 | 70.5 | B-2 | 7.0 | C-6 | 19.0 | P-6 | 3.5 |
| Polymer 34 | A-1 | 70.5 | B-3 | 7.0 | C-6 | 19.0 | P-1 | 3.5 |
| Polymer 35 | A-2 | 71.5 | B-4 | 6.0 | C-6 | 19.0 | P-3 | 3.5 |
| Polymer 36 | A-1 | 76.5 | B-2 | 7.0 | C-7 | 13.0 | P-1 | 3.5 |
| Polymer 37 | A-1 | 72.5 | B-2 | 7.0 | C-8 | 17.0 | P-1 | 3.5 |
| Polymer 38 | A-1 | 71.5 | B-2 | 10.0 | C-6 | 19.0 | — | — |
| Polymer 39 | A-2 | 69.0 | B-2 | 10.0 | C-6 | 21.0 | — | — |
| Polymer 40 | A-1 | 70.0 | B-1 | 10.0 | C-6 | 20.0 | — | — |
| Polymer 41 | A-1 | 67.0 | B-3 | 11.0 | C-6 | 22.0 | — | — |
| Polymer 42 | A-1 | 69.0 | B-4 | 11.0 | C-6 | 20.0 | — | — |
| Polymer 43 | A-1 | 75.0 | B-2 | 9.0 | C-7 | 16.0 | — | — |
| Polymer 44 | A-1 | 70.0 | B-2 | 9.0 | C-8 | 21.0 | — | — |
| Polymer 45 | A-2 | 70.0 | B-3 | 11.0 | C-6 | 19.0 | — | — |
| Polymer 46 | A-2 | 70.0 | B-4 | 11.0 | C-6 | 19.0 | — | — |

TABLE 3

| | Unit 1 | Introducing ratio (mol %) | Unit 2 | Introducing ratio (mol %) | Unit 3 | Introducing ratio (mol %) | Unit 4 | Introducing ratio (mol %) |
|---|---|---|---|---|---|---|---|---|
| Comparative Polymer 1 | A-1 | 75.5 | B-2 | 9.0 | — | — | P-1 | 3.5 |
| | | | B-5 | 12.0 | | | | |
| Comparative Polymer 2 | A-1 | 74.0 | B-1 | 10.5 | — | — | P-1 | 3.5 |
| | | | B-5 | 12.0 | | | | |
| Comparative Polymer 3 | A-1 | 69.5 | B-1 | 6.0 | C-5 | 21 | P-1 | 3.5 |
| Comparative Polymer 4 | A-1 | 69.5 | B-2 | 6.0 | C-5 | 21 | P-1 | 3.5 |
| Comparative Polymer 5 | A-1 | 76.0 | B-1 | 12.0 | — | — | — | — |
| | | | B-5 | 12.0 | | | | |
| Comparative Polymer 6 | A-1 | 70.0 | B-2 | 15.0 | — | — | — | — |
| | | | B-5 | 15.0 | | | | |
| Comparative Polymer 7 | A-1 | 60.0 | B-1 | 10.0 | C-5 | 30.0 | — | — |
| Comparative Polymer 8 | A-1 | 56.0 | B-2 | 10.0 | C-5 | 34.0 | — | — |

Structures of the repeating units (A-1 and A-2) introduced in the polymers are shown in Table 4. The repeating units (A-1 and A-2) satisfy the general formula (2).

TABLE 4

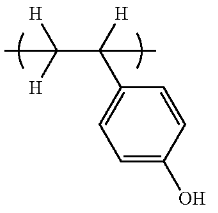

A-1

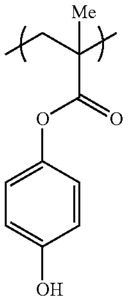

A-2

Structures of the repeating units (B-1 to B-5) introduced in the polymers are shown in Table 5. The repeating unit (B-1) satisfies the general formula (5), and the repeating unit (B-2) satisfies the general formula (4).

TABLE 5

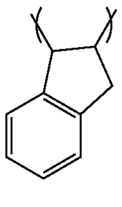

B-1

TABLE 5-continued

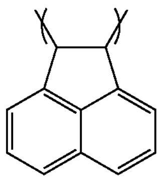

B-2

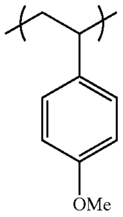

B-3

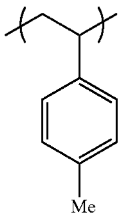

B-4

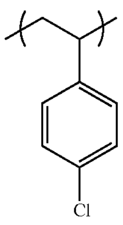

B-5

Structures of the repeating units (C-1 to C-8) introduced in the polymers are shown in Table 6. The repeating units (C-1 to C-4, C-6 to C-8) satisfy the general formula (1).

TABLE 6
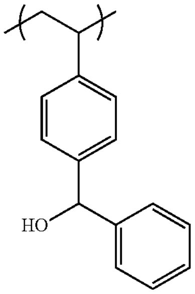
C-1
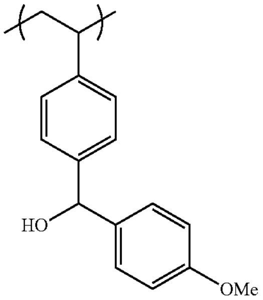
C-2
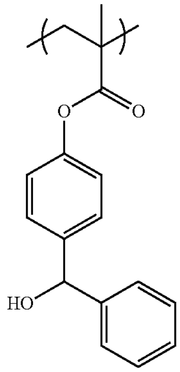
C-3
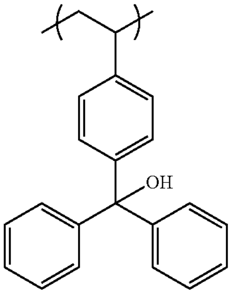
C-4
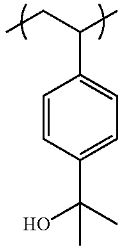
C-5
TABLE 6-continued
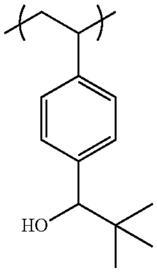
C-6
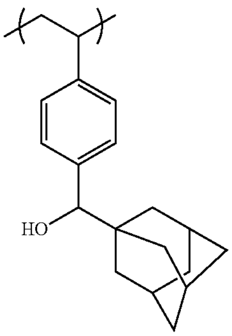
C-7
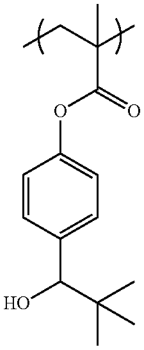
C-8
Structures of the repeating units (P-1 to P-6) introduced in the polymers are shown in Table 7. The repeating units (P-1, P-3, P-4, and P-5) satisfy the general formula (a2).
TABLE 7
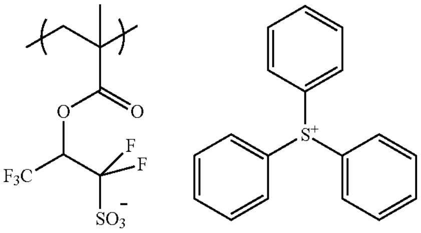
P-1

TABLE 7-continued

P-2

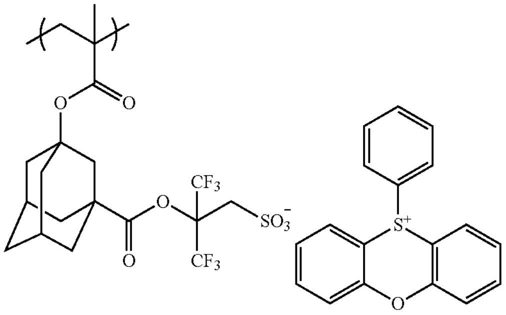

P-3

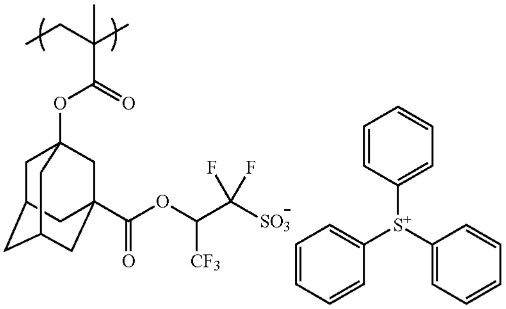

P-4

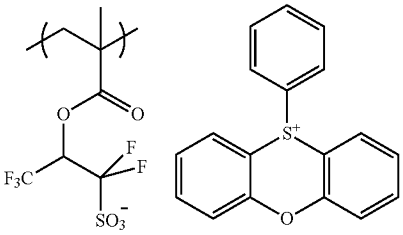

P-5

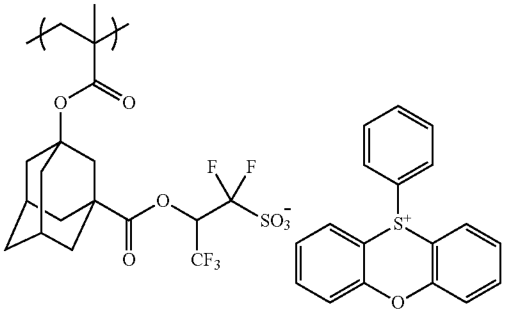

TABLE 7-continued

P-6

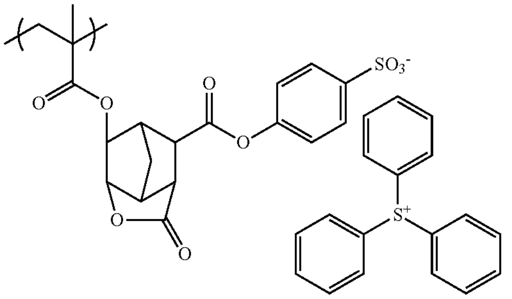

Examples 1 to 96 and Comparative Examples 1 to 10

Preparation of Negative Resist Composition

Examples 1 to 50 used the polymer compound of formula (1) where Rx and Ry are a hydrogen atom or (i) a monovalent aromatic group optionally containing a substituent, provided that Rx and Ry are not a hydrogen atom at the same time. Examples 51 to 96 used the polymer compound of formula (1) where Rx and Ry are a hydrogen atom or (ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms, provided that Rx and Ry are not a hydrogen atom at the same time. The synthesized polymers (Polymers 1 to 46 and Comparative polymers 1 to 8), acid generators (PAG-1 to 3), basic compounds (Q-1 to 3), and crosslinking agent TMGU (tetramethoxymethylglycoluril) or fluorine-containing polymer FP-1 for some compositions were dissolved in an organic solvent with the proportion shown in Tables 8 to 11 to prepare respective negative resist compositions. The negative resist compositions were each filtered through a 0.2-μm Teflon (registered trademark) filter to prepare solutions of the negative resist compositions. To each negative resist composition was added a surfactant, PF-636 (available from Omnova Solutions Inc.) in an amount of 0.075 part by mass with respect to the solid component.

Regarding the solvents in Tables 8 to 11, PGMEA denotes propylene glycol monomethyl ether acetate, EL denotes ethyl lactate, and PGME denotes propylene glycol monomethyl ether.

TABLE 8

| | Polymer compound | Acid generator | Basic compound | Additive | Solvent 1 | Solvent 2 | Solvent 3 |
|---|---|---|---|---|---|---|---|
| Example 1 | Polymer 1(80) | — | Q-1(4.0) | — | PGMEA(1080) | EL(1080) | PGME(1440) |
| Example 2 | Polymer 2(80) | — | Q-1(3.8) | — | PGMEA(1080) | EL(1080) | PGME(1440) |
| Example 3 | Polymer 3(80) | — | Q-1(4.1) | — | PGMEA(1080) | EL(1080) | PGME(1440) |
| Example 4 | Polymer 4(80) | — | Q-1(3.9) | — | PGMEA(1080) | EL(1080) | PGME(1440) |
| Example 5 | Polymer 5(80) | — | Q-1(4.0) | — | PGMEA(1080) | EL(1080) | PGME(1440) |
| Example 6 | Polymer 6(80) | — | Q-1(4.0) | — | PGMEA(1080) | EL(1080) | PGME(1440) |
| Example 7 | Polymer 7(80) | — | Q-1(4.2) | — | PGMEA(1080) | EL(1080) | PGME(1440) |
| Example 8 | Polymer 8(80) | — | Q-1(3.8) | — | PGMEA(1080) | EL(1080) | PGME(1440) |
| Example 9 | Polymer 9(80) | — | Q-1(4.3) | — | PGMEA(1080) | EL(1080) | PGME(1440) |
| Example 10 | Polymer 10(80) | — | Q-1(3.6) | — | PGMEA(1080) | EL(1080) | PGME(1440) |
| Example 11 | Polymer 11(80) | — | Q-1(3.8) | — | PGMEA(1080) | EL(1080) | PGME(1440) |
| Example 12 | Polymer 12(80) | — | Q-1(3.9) | — | PGMEA(1080) | EL(1080) | PGME(1440) |
| Example 13 | Polymer 13(80) | — | Q-1(4.1) | — | PGMEA(1080) | EL(1080) | PGME(1440) |

TABLE 8-continued

| | Polymer compound | Acid generator | Basic compound | Additive | Solvent 1 | Solvent 2 | Solvent 3 |
|---|---|---|---|---|---|---|---|
| Example 14 | Polymer 14(80) | — | Q-1(4.0) | — | PGMEA(1080) | EL(1080) | PGME(1440) |
| Example 15 | Polymer 15(80) | PAG-1(8.0) | Q-1(4.0) | — | PGMEA(1080) | EL(1080) | PGME(1440) |
| Example 16 | Polymer 16(80) | PAG-1(8.0) | Q-1(4.2) | — | PGMEA(1080) | EL(1080) | PGME(1440) |
| Example 17 | Polymer 17(80) | PAG-1(8.0) | Q-1(3.8) | — | PGMEA(1080) | EL(1080) | PGME(1440) |
| Example 18 | Polymer 18(80) | PAG-1(8.0) | Q-1(3.9) | — | PGMEA(1080) | EL(1080) | PGME(1440) |
| Example 19 | Polymer 19(80) | PAG-1(8.0) | Q-1(4.0) | — | PGMEA(1080) | EL(1080) | PGME(1440) |
| Example 20 | Polymer 20(80) | PAG-1(8.0) | Q-1(4.1) | — | PGMEA(1080) | EL(1080) | PGME(1440) |
| Example 21 | Polymer 21(80) | PAG-1(8.0) | Q-1(3.9) | — | PGMEA(1080) | EL(1080) | PGME(1440) |
| Example 22 | Polymer 22(80) | PAG-1(8.0) | Q-1(4.2) | — | PGMEA(1080) | EL(1080) | PGME(1440) |
| Example 23 | Polymer 23(80) | PAG-1(8.0) | Q-1(4.1) | — | PGMEA(1080) | EL(1080) | PGME(1440) |
| Example 24 | Polymer 24(80) | PAG-1(8.0) | Q-1(3.9) | — | PGMEA(1080) | EL(1080) | PGME(1440) |
| Example 25 | Polymer 1(80) | PAG-1(5.0) | Q-1(4.1) | — | PGMEA(1080) | EL(1080) | PGME(1440) |
| Example 26 | Polymer 1(80) | PAG-2(5.0) | Q-1(4.3) | — | PGMEA(1080) | EL(1080) | PGME(1440) |
| Example 27 | Polymer 1(80) | PAG-3(5.0) | Q-1(4.2) | — | PGMEA(1080) | EL(1080) | PGME(1440) |
| Example 28 | Polymer 1(80) | PAG-1(5.0) | Q-2(4.1) | — | PGMEA(1080) | EL(1080) | PGME(1440) |
| Example 29 | Polymer 1(80) | PAG-1(5.2) | Q-3(4.0) | — | PGMEA(1080) | EL(1080) | PGME(1440) |
| Example 30 | Polymer 1(40)<br>Polymer 15(40) | — | Q-1(4.0) | — | PGMEA(1080) | EL(1080) | PGME(1440) |

TABLE 9

| | Polymer compound | Acid generator | Basic compound | Additive | Solvent 1 | Solvent 2 | Solvent 3 |
|---|---|---|---|---|---|---|---|
| Example 31 | Polymer 1(40)<br>Polymer 15(40) | PAG-1(5.0) | Q-1(4.6) | — | PGMEA(1080) | EL(1080) | PGME(1440) |
| Example 32 | Polymer 2(40)<br>Polymer 16(40) | PAG-1(5.0) | Q-2(4.4) | — | PGMEA(1080) | EL(1080) | PGME(1440) |
| Example 33 | Polymer 2(40)<br>Polymer 16(40) | PAG-1(5.0) | Q-3(4.3) | — | PGMEA(1080) | EL(1080) | PGME(1440) |
| Example 34 | Polymer 1(40)<br>Polymer 15(40) | PAG-2(5.0) | Q-1(4.1) | — | PGMEA(1080) | EL(1080) | PGME(1440) |
| Example 35 | Polymer 1(40)<br>Polymer 15(40) | PAG-3(5.0) | Q-1(4.5) | — | PGMEA(1080) | EL(1080) | PGME(1440) |
| Example 36 | Polymer 2(40)<br>Polymer 16(40) | PAG-1(5.0) | Q-1(4.7) | — | PGMEA(1080) | EL(1080) | PGME(1440) |
| Example 37 | Polymer 3(40)<br>Polymer 17(40) | PAG-1(5.0) | Q-1(4.7) | — | PGMEA(1080) | EL(1080) | PGME(1440) |
| Example 38 | Polymer 10(40)<br>Polymer 18(40) | PAG-1(5.0) | Q-1(4.6) | — | PGMEA(1080) | EL(1080) | PGME(1440) |
| Example 39 | Polymer 11(40)<br>Polymer 19(40) | PAG-1(5.0) | Q-1(4.7) | — | PGMEA(1080) | EL(1080) | PGME(1440) |
| Example 40 | Polymer 12(40)<br>Polymer 20(40) | PAG-1(5.0) | Q-1(4.9) | — | PGMEA(1080) | EL(1080) | PGME(1440) |
| Example 41 | Polymer 13(40)<br>Polymer 21(40) | PAG-1(5.0) | Q-1(5.0) | — | PGMEA(1080) | EL(1080) | PGME(1440) |
| Example 42 | Polymer 14(40)<br>Polymer 22(40) | PAG-1(5.0) | Q-1(5.2) | — | PGMEA(1080) | EL(1080) | PGME(1440) |
| Example 43 | Polymer 10(40)<br>Polymer 23(40) | PAG-1(5.0) | Q-1(5.1) | — | PGMEA(1080) | EL(1080) | PGME(1440) |
| Example 44 | Polymer 11(40)<br>Polymer 24(40) | PAG-1(5.0) | Q-1(4.9) | — | PGMEA(1080) | EL(1080) | PGME(1440) |
| Example 45 | Polymer 12(40)<br>Polymer 24(40) | PAG-1(5.0) | Q-1(5.0) | — | PGMEA(1080) | EL(1080) | PGME(1440) |
| Example 46 | Polymer 11(40)<br>Polymer 22(40) | PAG-1(5.0) | Q-1(5.0) | — | PGMEA(1080) | EL(1080) | PGME(1440) |
| Example 47 | Polymer 13(40)<br>Polymer 15(40) | PAG-1(5.0) | Q-1(4.9) | — | PGMEA(1080) | EL(1080) | PGME(1440) |
| Example 48 | Polymer 1(80) | — | Q-1(4.1) | FP-1(3.0) | PGMEA(1080) | EL(1080) | PGME(1440) |
| Example 49 | Polymer 1(40)<br>Polymer 15(40) | — | Q-1(4.6) | FP-1(3.0) | PGMEA(1080) | EL(1080) | PGME(1440) |
| Example 50 | Polymer 1(40)<br>Polymer 15(40) | PAG-1(5.0) | Q-1(4.8) | FP-1(3.0) | PGMEA(1080) | EL(1080) | PGME(1440) |

TABLE 10

| | Polymer compound | Acid generator | Basic compound | Additive | Solvent 1 | Solvent 2 | Solvent 3 |
|---|---|---|---|---|---|---|---|
| Example 51 | Polymer 25(80) | — | Q-1(1.5) | — | PGMEA(1080) | EL(1080) | PGME(1440) |
| Example 52 | Polymer 26(80) | — | Q-1(1.7) | — | PGMEA(1080) | EL(1080) | PGME(1440) |
| Example 53 | Polymer 27(80) | — | Q-1(1.6) | — | PGMEA(1080) | EL(1080) | PGME(1440) |
| Example 54 | Polymer 28(80) | — | Q-1(1.7) | — | PGMEA(1080) | EL(1080) | PGME(1440) |
| Example 55 | Polymer 29(80) | — | Q-1(1.8) | — | PGMEA(1080) | EL(1080) | PGME(1440) |
| Example 56 | Polymer 30(80) | — | Q-1(1.5) | — | PGMEA(1080) | EL(1080) | PGME(1440) |
| Example 57 | Polymer 31(80) | — | Q-1(1.7) | — | PGMEA(1080) | EL(1080) | PGME(1440) |
| Example 58 | Polymer 32(80) | — | Q-1(1.9) | — | PGMEA(1080) | EL(1080) | PGME(1440) |
| Example 59 | Polymer 33(80) | — | Q-1(1.5) | — | PGMEA(1080) | EL(1080) | PGME(1440) |
| Example 60 | Polymer 34(80) | — | Q-1(1.8) | — | PGMEA(1080) | EL(1080) | PGME(1440) |
| Example 61 | Polymer 35(80) | — | Q-1(1.5) | — | PGMEA(1080) | EL(1080) | PGME(1440) |
| Example 62 | Polymer 36(80) | — | Q-1(1.9) | — | PGMEA(1080) | EL(1080) | PGME(1440) |
| Example 63 | Polymer 37(80) | — | Q-1(1.5) | — | PGMEA(1080) | EL(1080) | PGME(1440) |
| Example 64 | Polymer 38(80) | PAG-1(8.0) | Q-1(1.9) | — | PGMEA(1080) | EL(1080) | PGME(1440) |
| Example 65 | Polymer 39(80) | PAG-1(8.0) | Q-1(1.5) | — | PGMEA(1080) | EL(1080) | PGME(1440) |
| Example 66 | Polymer 40(80) | PAG-1(8.0) | Q-1(1.9) | — | PGMEA(1080) | EL(1080) | PGME(1440) |
| Example 67 | Polymer 41(80) | PAG-1(8.0) | Q-1(1.9) | — | PGMEA(1080) | EL(1080) | PGME(1440) |
| Example 68 | Polymer 42(80) | PAG-1(8.0) | Q-1(1.5) | — | PGMEA(1080) | EL(1080) | PGME(1440) |
| Example 69 | Polymer 43(80) | PAG-1(8.0) | Q-1(1.8) | — | PGMEA(1080) | EL(1080) | PGME(1440) |
| Example 70 | Polymer 44(80) | PAG-1(8.0) | Q-1(1.5) | — | PGMEA(1080) | EL(1080) | PGME(1440) |
| Example 71 | Polymer 45(80) | PAG-1(8.0) | Q-1(1.7) | — | PGMEA(1080) | EL(1080) | PGME(1440) |
| Example 72 | Polymer 46(80) | PAG-1(8.0) | Q-1(1.5) | — | PGMEA(1080) | EL(1080) | PGME(1440) |
| Example 73 | Polymer 25(80) | PAG-1(5.0) | Q-1(1.9) | — | PGMEA(1080) | EL(1080) | PGME(1440) |
| Example 74 | Polymer 25(80) | PAG-2(5.0) | Q-1(1.8) | — | PGMEA(1080) | EL(1080) | PGME(1440) |
| Example 75 | Polymer 25(80) | PAG-3(5.0) | Q-1(1.5) | — | PGMEA(1080) | EL(1080) | PGME(1440) |
| Example 76 | Polymer 25(80) | PAG-1(5.0) | Q-1(1.8) | — | PGMEA(1080) | EL(1080) | PGME(1440) |
| Example 77 | Polymer 25(80) | PAG-1(5.2) | Q-1(1.5) | — | PGMEA(1080) | EL(1080) | PGME(1440) |
| Example 78 | Polymer 25(40)<br>Polymer 38(40) | — | Q-1(1.9) | — | PGMEA(1080) | EL(1080) | PGME(1440) |
| Example 79 | Polymer 25(40)<br>Polymer 38(40) | PAG-1(5.0) | Q-1(1.5) | — | PGMEA(1080) | EL(1080) | PGME(1440) |
| Example 80 | Polymer 26(40)<br>Polymer 39(40) | PAG-1(5.0) | Q-1(1.7) | — | PGMEA(1080) | EL(1080) | PGME(1440) |
| Example 81 | Polymer 26(40)<br>Polymer 39(40) | PAG-1(5.0) | Q-1(1.5) | — | PGMEA(1080) | EL(1080) | PGME(1440) |
| Example 82 | Polymer 25(40)<br>Polymer 38(40) | PAG-2(5.0) | Q-1(1.7) | — | PGMEA(1080) | EL(1080) | PGME(1440) |
| Example 83 | Polymer 25(40)<br>Polymer 38(40) | PAG-3(5.0) | Q-1(1.5) | — | PGMEA(1080) | EL(1080) | PGME(1440) |
| Example 84 | Polymer 26(40)<br>Polymer 39(40) | PAG-1(5.0) | Q-1(1.7) | — | PGMEA(1080) | EL(1080) | PGME(1440) |
| Example 85 | Polymer 27(40)<br>Polymer 38(40) | PAG-1(5.0) | Q-1(1.5) | — | PGMEA(1080) | EL(1080) | PGME(1440) |
| Example 86 | Polymer 27(40)<br>Polymer 40(40) | PAG-1(5.0) | Q-1(1.7) | — | PGMEA(1080) | EL(1080) | PGME(1440) |
| Example 87 | Polymer 35(40)<br>Polymer 46(40) | PAG-1(5.0) | Q-1(1.5) | — | PGMEA(1080) | EL(1080) | PGME(1440) |
| Example 88 | Polymer 36(40)<br>Polymer 43(40) | PAG-1(5.0) | Q-1(1.5) | — | PGMEA(1080) | EL(1080) | PGME(1440) |
| Example 89 | Polymer 37(40)<br>Polymer 44(40) | PAG-1(5.0) | Q-1(1.8) | — | PGMEA(1080) | EL(1080) | PGME(1440) |
| Example 90 | Polymer 35(40)<br>Polymer 39(40) | PAG-1(5.0) | Q-1(1.5) | — | PGMEA(1080) | EL(1080) | PGME(1440) |
| Example 91 | Polymer 36(40)<br>Polymer 39(40) | PAG-1(5.0) | Q-1(1.5) | — | PGMEA(1080) | EL(1080) | PGME(1440) |
| Example 92 | Polymer 37(40)<br>Polymer 39(40) | PAG-1(5.0) | Q-1(2.0) | — | PGMEA(1080) | EL(1080) | PGME(1440) |
| Example 93 | Polymer 37(40)<br>Polymer 38(40) | PAG-1(5.0) | Q-1(1.7) | — | PGMEA(1080) | EL(1080) | PGME(1440) |
| Example 94 | Polymer 25(80) | — | Q-1(1.9) | FP-1(3.0) | PGMEA(1080) | EL(1080) | PGME(1440) |
| Example 95 | Polymer 25(40)<br>Polymer 38(40) | — | Q-1(2.0) | FP-1(3.0) | PGMEA(1080) | EL(1080) | PGME(1440) |
| Example 96 | Polymer 25(40)<br>Polymer 38(40) | PAG-1(5.0) | Q-1(1.7) | FP-1(3.0) | PGMEA(1080) | EL(1080) | PGME(1440) |

TABLE 11

| | Polymer compound | Acid generator | Basic compound | Additive | Solvent 1 | Solvent 2 | Solvent 3 |
|---|---|---|---|---|---|---|---|
| Comparative Example 1 | Comparative Polymer 1(80) | — | Q-1(4.0) | TMGU(8.0) | PGMEA(1080) | EL(1080) | PGME(1440) |
| Comparative Example 2 | Comparative Polymer 2(80) | — | Q-1(4.1) | TMGU(8.0) | PGMEA(1080) | EL(1080) | PGME(1440) |
| Comparative Example 3 | Comparative Polymer 3(80) | — | Q-1(4.2) | — | PGMEA(1080) | EL(1080) | PGME(1440) |
| Comparative Example 4 | Comparative Polymer 4(80) | — | Q-1(4.4) | — | PGMEA(1080) | EL(1080) | PGME(1440) |
| Comparative Example 5 | Comparative Polymer 5(80) | PAG-1(5.0) | Q-1(4.8) | TMGU(8.0) | PGMEA(1080) | EL(1080) | PGME(1440) |
| Comparative Example 6 | Comparative Polymer 6(80) | PAG-1(5.0) | Q-1(4.7) | TMGU(8.0) | PGMEA(1080) | EL(1080) | PGME(1440) |
| Comparative Example 7 | Comparative Polymer 7(80) | PAG-1(5.0) | Q-1(4.6) | — | PGMEA(1080) | EL(1080) | PGME(1440) |
| Comparative Example 8 | Comparative Polymer 8(80) | PAG-1(5.0) | Q-1(4.2) | — | PGMEA(1080) | EL(1080) | PGME(1440) |
| Comparative Example 9 | Comparative Polymer 3(40) Comparative Polymer 7(40) | PAG-1(5.0) | Q-1(4.7) | — | PGMEA(1080) | EL(1080) | PGME(1440) |
| Comparative Example 10 | Comparative Polymer 4(40) Comparative Polymer 8(40) | PAG-1(5.0) | Q-1(5.0) | — | PGMEA(1080) | EL(1080) | PGME(1440) |

Structures of the used acid generators (PAG-1 to 3) are shown in Table 12.

TABLE 12

PAG-1

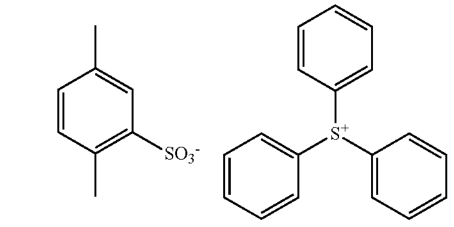

PAG-2

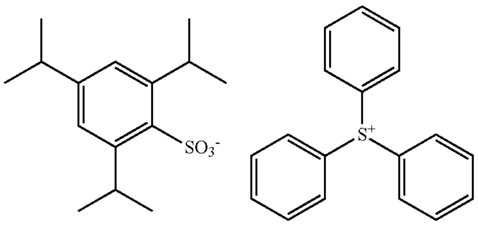

PAG-3

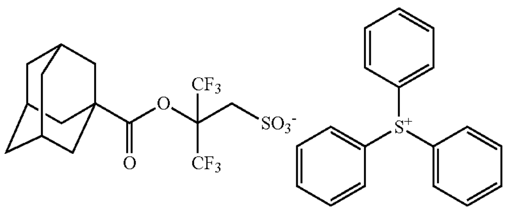

Structures of the used basic compounds (Q-1 to 3) are shown in Table 13.

TABLE 13

Q-1

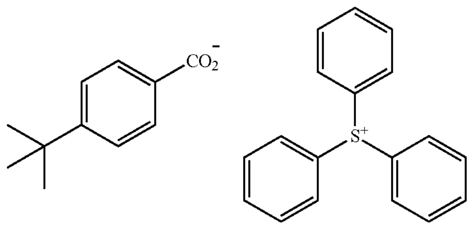

Q-2

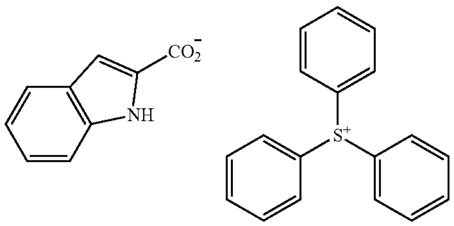

Q-3

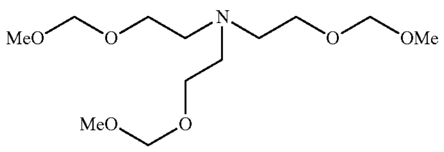 [SMILES: COCOCCN(CCOCOC)CCOCOC]

A structure of the used fluorine-containing polymer (FP-1) is shown below.

FP-1

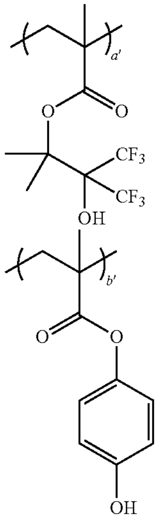

($a'$ = 0.80, $b'$ = 0.20, Mw = 6,000)

Electron Beam Lithography Evaluation (1) Resolution Evaluation

The prepared negative resist compositions (Examples 1 to 96 and Comparative Examples 1 to 10) were each applied onto a 152-mm square mask blank having a chromium oxynitride film on its outermost surface by spin coating with ACT-M (manufactured by Tokyo Electron, Ltd.), and pre-baked on a hot plate at 110° C. for 600 seconds to form a resist film with a thickness of 80 nm. The thickness of the obtained resist film was measured with an optical measurement apparatus Nanospec (manufactured by Nanometrics, Inc.). The measurement was performed at 81 in-plane positions of the blank substrate except for an outer edge portion within 10 mm from the blank outer circumference to calculate the average film thickness value and the film thickness range.

Then, the resist film was exposed to light with an electron beam exposure apparatus (EBM-5000plus, manufactured by NuFlare Technology, Inc. with an acceleration voltage of 50 keV), baked (PEB, post exposure bake) at 130° C. for 600 seconds, and developed with a 2.38 mass % tetramethylammonium hydroxide aqueous solution to obtain a negative pattern. The obtained resist pattern was evaluated in the following manner.

The blank having the formed pattern was observed with a top-down SEM (scanning electron microscope). An exposure dose that achieved 1:1 resolution of 400-nm 1:1 line and space (LS) was defined as optimum exposure dose ($\mu C/cm^2$). A minimum dimension at the exposure dose that achieves 1:1 resolution of 400-nm line and space was defined as resolution (limiting resolution). LER of a 200-nm LS was measured with SEM. Moreover, the limiting resolutions of an isolated line (IL) and an isolated space (IS) were also measured. IL is resolution of one isolated line pattern, and IS is resolution of one isolated space pattern. Tables 14 to 17 show evaluation results of the inventive negative resist compositions and the comparative negative compositions in electron beam lithography. Incidentally, the optimum exposure dose shown in Tables 14 to 17 is a value on the basis of LS.

TABLE 14

| | Optimum exposure dose (LS) ($\mu C/cm^2$) | Resolution (LS) (nm) | Resolution (IL) (nm) | Resolution (IS) (nm) | LER (nm) |
|---|---|---|---|---|---|
| Example 1 | 47 | 40 | 40 | 40 | 4.6 |
| Example 2 | 49 | 45 | 40 | 40 | 4.7 |
| Example 3 | 48 | 45 | 45 | 40 | 4.8 |
| Example 4 | 50 | 40 | 45 | 45 | 4.8 |
| Example 5 | 47 | 40 | 45 | 40 | 4.7 |
| Example 6 | 46 | 45 | 40 | 45 | 4.9 |
| Example 7 | 49 | 40 | 45 | 40 | 4.6 |
| Example 8 | 48 | 45 | 40 | 40 | 4.8 |
| Example 9 | 47 | 40 | 45 | 45 | 4.7 |
| Example 10 | 50 | 45 | 45 | 40 | 4.9 |
| Example 11 | 51 | 45 | 40 | 45 | 4.8 |
| Example 12 | 50 | 40 | 45 | 45 | 4.7 |
| Example 13 | 49 | 45 | 40 | 40 | 4.8 |
| Example 14 | 46 | 45 | 45 | 40 | 5.0 |
| Example 15 | 48 | 40 | 40 | 45 | 4.8 |
| Example 16 | 47 | 45 | 40 | 45 | 4.7 |
| Example 17 | 47 | 40 | 45 | 45 | 4.9 |
| Example 18 | 49 | 40 | 40 | 40 | 4.8 |
| Example 19 | 47 | 45 | 45 | 40 | 4.7 |
| Example 20 | 48 | 40 | 40 | 45 | 4.8 |
| Example 21 | 48 | 45 | 45 | 40 | 4.7 |
| Example 22 | 48 | 40 | 45 | 45 | 4.7 |
| Example 23 | 50 | 40 | 40 | 40 | 4.8 |
| Example 24 | 49 | 40 | 45 | 45 | 4.6 |
| Example 25 | 49 | 45 | 45 | 40 | 4.9 |
| Example 26 | 48 | 40 | 45 | 45 | 4.8 |
| Example 27 | 47 | 45 | 40 | 40 | 4.7 |
| Example 28 | 49 | 45 | 40 | 40 | 4.8 |
| Example 29 | 48 | 45 | 45 | 45 | 4.9 |
| Example 30 | 49 | 40 | 45 | 40 | 4.7 |

TABLE 15

| | Optimum exposure dose (LS) ($\mu C/cm^2$) | Resolution (LS) (nm) | Resolution (IL) (nm) | Resolution (IS) (nm) | LER (nm) |
|---|---|---|---|---|---|
| Example 31 | 49 | 45 | 40 | 45 | 4.6 |
| Example 32 | 48 | 40 | 45 | 45 | 4.8 |
| Example 33 | 47 | 45 | 40 | 45 | 4.7 |
| Example 34 | 46 | 40 | 40 | 45 | 4.6 |
| Example 35 | 52 | 40 | 40 | 45 | 4.8 |
| Example 36 | 48 | 45 | 40 | 40 | 4.9 |
| Example 37 | 48 | 45 | 45 | 45 | 4.7 |
| Example 38 | 49 | 40 | 45 | 45 | 4.8 |
| Example 39 | 47 | 45 | 40 | 45 | 4.8 |
| Example 40 | 48 | 40 | 40 | 45 | 4.8 |
| Example 41 | 46 | 45 | 40 | 40 | 4.6 |
| Example 42 | 49 | 45 | 45 | 45 | 4.7 |
| Example 43 | 48 | 40 | 40 | 45 | 4.8 |
| Example 44 | 48 | 40 | 45 | 40 | 4.9 |
| Example 45 | 47 | 40 | 40 | 45 | 4.7 |
| Example 46 | 47 | 45 | 45 | 45 | 4.8 |
| Example 47 | 48 | 40 | 40 | 45 | 5.0 |
| Example 48 | 49 | 40 | 45 | 40 | 4.7 |
| Example 49 | 47 | 40 | 40 | 45 | 4.9 |
| Example 50 | 48 | 40 | 45 | 40 | 4.8 |

TABLE 16

| | Optimum exposure dose (LS) ($\mu C/cm^2$) | Resolution (LS) (nm) | Resolution (IL) (nm) | Resolution (IS) (nm) | LER (nm) |
|---|---|---|---|---|---|
| Example 51 | 47 | 40 | 40 | 40 | 4.6 |
| Example 52 | 50 | 40 | 40 | 40 | 4.9 |
| Example 53 | 48 | 40 | 40 | 40 | 4.8 |
| Example 54 | 49 | 45 | 45 | 45 | 4.9 |

TABLE 16-continued

| | Optimum exposure dose (LS) (μC/cm$^2$) | Resolution (LS) (nm) | Resolution (IL) (nm) | Resolution (IS) (nm) | LER (nm) |
|---|---|---|---|---|---|
| Example 55 | 48 | 40 | 40 | 40 | 4.6 |
| Example 56 | 51 | 45 | 45 | 45 | 4.7 |
| Example 57 | 47 | 40 | 40 | 45 | 4.9 |
| Example 58 | 49 | 45 | 45 | 40 | 4.7 |
| Example 59 | 47 | 45 | 40 | 45 | 4.9 |
| Example 60 | 49 | 40 | 45 | 45 | 4.8 |
| Example 61 | 50 | 45 | 45 | 45 | 4.9 |
| Example 62 | 50 | 40 | 40 | 40 | 4.7 |
| Example 63 | 48 | 45 | 45 | 45 | 4.8 |
| Example 64 | 49 | 40 | 45 | 40 | 4.6 |
| Example 65 | 50 | 45 | 40 | 45 | 4.7 |
| Example 66 | 50 | 45 | 40 | 45 | 4.8 |
| Example 67 | 51 | 40 | 45 | 45 | 4.9 |
| Example 68 | 49 | 45 | 40 | 40 | 4.8 |
| Example 69 | 48 | 40 | 45 | 45 | 4.7 |
| Example 70 | 47 | 45 | 40 | 40 | 4.9 |
| Example 71 | 48 | 40 | 45 | 40 | 4.8 |
| Example 72 | 49 | 45 | 45 | 40 | 4.7 |
| Example 73 | 46 | 40 | 40 | 45 | 4.8 |
| Example 74 | 47 | 45 | 45 | 45 | 4.9 |
| Example 75 | 47 | 40 | 40 | 45 | 4.7 |
| Example 76 | 47 | 40 | 45 | 40 | 4.6 |
| Example 77 | 48 | 40 | 40 | 40 | 4.9 |
| Example 78 | 49 | 40 | 40 | 40 | 4.6 |
| Example 79 | 49 | 40 | 40 | 40 | 4.8 |
| Example 80 | 50 | 45 | 45 | 45 | 4.9 |
| Example 81 | 48 | 40 | 45 | 40 | 4.7 |
| Example 82 | 47 | 45 | 40 | 45 | 4.8 |
| Example 83 | 48 | 40 | 45 | 40 | 4.9 |
| Example 84 | 48 | 45 | 45 | 40 | 4.8 |
| Example 85 | 47 | 40 | 40 | 40 | 4.8 |
| Example 86 | 49 | 40 | 40 | 45 | 4.8 |
| Example 87 | 50 | 45 | 45 | 45 | 4.7 |
| Example 88 | 47 | 40 | 40 | 40 | 4.9 |
| Example 89 | 46 | 40 | 45 | 40 | 4.8 |
| Example 90 | 48 | 45 | 40 | 40 | 4.7 |
| Example 91 | 47 | 40 | 40 | 40 | 4.9 |
| Example 92 | 47 | 40 | 45 | 45 | 4.6 |
| Example 93 | 48 | 45 | 45 | 45 | 4.9 |
| Example 94 | 49 | 40 | 40 | 45 | 4.7 |
| Example 95 | 49 | 45 | 40 | 40 | 4.8 |
| Example 96 | 50 | 45 | 45 | 45 | 4.8 |

TABLE 17

| | Optimum exposure dose (LS) (μC/cm$^2$) | Resolution (LS) (nm) | Resolution (IL) (nm) | Resolution (IS) (nm) | LER (nm) |
|---|---|---|---|---|---|
| Comparative Example 1 | 51 | 55 | 60 | 60 | 6.2 |
| Comparative Example 2 | 50 | 55 | 55 | 60 | 6.8 |
| Comparative Example 3 | 49 | 40 | 40 | 45 | 4.9 |
| Comparative Example 4 | 47 | 45 | 40 | 40 | 4.9 |
| Comparative Example 5 | 48 | 60 | 55 | 60 | 6.4 |
| Comparative Example 6 | 49 | 55 | 55 | 60 | 6.1 |
| Comparative Example 7 | 48 | 50 | 50 | 50 | 5.8 |
| Comparative Example 8 | 47 | 50 | 50 | 50 | 5.7 |
| Comparative Example 9 | 48 | 40 | 40 | 40 | 4.7 |
| Comparative Example 10 | 47 | 40 | 45 | 40 | 4.7 |

(2) Defect Evaluation

The prepared negative resist compositions (Examples 1, 3, 15, 17, 31, 37, 51, 53, 64, 66, 79, 85 and Comparative Examples 7, 8) were each used to form a pattern at the center of the substrate under the same condition as in (1) resolution evaluation. After exposure and development, unexposed parts were inspected with a mask defect inspection apparatus (M2351, manufactured by Lasertec Inc.) to observe whether a radial development residue remained on the chromium film. The results are given in Tables 18 to 20.

TABLE 18

| | Radial defect |
|---|---|
| Example 1 | None |
| Example 3 | None |
| Example 15 | None |
| Example 17 | None |
| Example 31 | None |
| Example 37 | None |

TABLE 19

| | Radial defect |
|---|---|
| Example 51 | None |
| Example 53 | None |
| Example 64 | None |
| Example 66 | None |
| Example 79 | None |
| Example 85 | None |

TABLE 20

| | Radial defect |
|---|---|
| Comparative Example 7 | Yes |
| Comparative Example 8 | Yes |

The results in Tables 14 to 20 will be explained. As shown in Tables 14 to 16, all the negative resist compositions according to the invention resulted in good resolution and line edge roughness. By contrast, the negative resist compositions containing the crosslinking agent in Comparative Examples 1, 2, 5, and 6 had poor resolution as shown in Table 17.

Moreover, when the inventive negative resist compositions were used, no radial defect was observed and excellent defect performance was achieved as shown in Tables 18 and 19, while the negative resist compositions in comparative examples 7 and 8 caused a radial defect in the defect inspection, despite a moderate good resolution, as shown in Table 20. The reason is considered as follows. The polymers used in Comparative Examples induced crosslinking of the exposed part by an effect of acid and produced dehydrated polymers. Because the dehydrated polymers have low solubility in the developer, the dehydrated polymers produced from the exposed part were not completely removed by the development and remained on the substrate after completion of the development, consequently causing the radial defect. By contrast, the polymers used in Examples have a structure that does not cause the dehydration reaction and undergoes only the crosslinking reaction. Therefore, the polymers were not dissolved from the exposed part, and the radial defect was not caused.

As can be seen from the above explanation, use of the inventive negative resist composition enables the formation of a pattern with high resolution and small line edge roughness. Moreover, this composition advantageously causes no development defect and thus the patterning process using the same is useful in photolithography for processing photomask blanks, which particularly require that the number of defects is small.

(3) EB Exposure Evaluation of Resist Film on which Antistatic Film is Formed (Reference Examples 1 to 6)

If a high current of 50 A or more, especially 200 A or more, is applied for drawing on a resist film with an electron beam, an orbit of the electron beam is bent by electrostatic repulsion due to the charged resist film. This can cause a problem of inability to draw a pattern with high position accuracy. To solve this problem, an antistatic film was formed on the resist film before pattern drawing.

A resist film was formed under the same condition as in (I) resolution evaluation. Then, a conductive polymer composition was dropped and applied over the resist film by spin coating with ACT-M (manufactured by Tokyo Electron, Ltd.), and baked on a hot plate at 90° C. for 600 seconds to form an antistatic film with a thickness of 60 nm. The conductive polymer composition used was an aqueous dispersion containing polyaniline doped with polystyrene sulfonic acid, described in Proc. SPIE Vol. 8522 85220O-1. The photomask blank having this antistatic film on the resist layer was exposed to light with an electron beam exposure apparatus (EBM-5000plus, manufactured by NuFlare Technology, Ltd., with acceleration voltage of 50 keV), baked (PEB, post exposure bake) at 130° C. for 600 seconds, and developed with a 2.38 mass % tetramethylammonium hydroxide aqueous solution to obtain a negative pattern. The obtained resist pattern was then evaluated in the following manner.

<Optimum Exposure Dose, Limiting Resolution>

These properties were evaluated in the same manner as in (I) resolution evaluation.

<Surface Resistivity>

The surface resistivity of the obtained antistatic film and the resist film was measured with Hiresta-UP MCP-HT450 (manufactured by Mitsubishi Chemical corp.).

<Sensitivity Change Rate>

The sensitivities in Reference Examples 1 to 6 were respectively compared with those in Examples 1, 30, 31, 48, 49, and 50 to calculate deviation (%).

<Pattern Profile>

The pattern portion was cut to take a SEM image, and the image was visually checked.

<PCD (Post Coating Delay)>

The film was exposed 2 weeks after forming the antistatic film, with the same exposure dose as the exposure dose that achieved the resolution of a 400-nm line and space pattern just after forming the antistatic film to measure a difference in line width. The change amount of the line width per day was defined as PCD.

The results are given in Table 21.

TABLE 21

| | Negative resist composition | Optimum exposure dose ($\mu C/cm^2$) | Limiting resolution (nm) | Surface resistance ($\Omega/\square$) | Sensitivity change rate | Pattern profile | PCD (nm/day) |
|---|---|---|---|---|---|---|---|
| Reference Example 1 | Example 1 | 41 | 55 | $3.0 \times 10^8$ | −14.58% | Negative tapered | 0.29 |
| Reference Example 2 | Example 30 | 43 | 55 | $3.3 \times 10^8$ | −8.51% | Negative tapered | 0.48 |
| Reference Example 3 | Example 31 | 43 | 55 | $3.2 \times 10^8$ | −7.84% | Negative tapered | 0.34 |
| Reference Example 4 | Example 48 | 46 | 45 | $3.0 \times 10^8$ | −2.08% | Rectangular | 0.07 |
| Reference Example 5 | Example 49 | 48 | 45 | $3.1 \times 10^8$ | −2.13% | Rectangular | 0.07 |
| Reference Example 6 | Example 50 | 48 | 45 | $3.2 \times 10^8$ | −1.96% | Rectangular | 0.07 |

As shown in Table 21, in Reference Examples 1 to 3, which used the negative resist composition not containing a fluorine-containing resin, acid components contained in the antistatic film composition penetrated into the resist film. This penetration caused the sensitivity to be considerably changed, the pattern profile to be negatively tapered, and the PCD to be increased. By contrast, in Reference Examples 4 to 6, which used the negative resist composition containing a fluorine-containing resin, the sensitivity was less changed, the pattern profile was kept rectangular, and the PCD was good. With respect to the surface resistivity, there is no much difference among Reference Examples 1 to 6, and all examples could draw the pattern with high drawing position accuracy.

These results indicate that the negative resist composition containing a fluorine-containing resin is preferably used for drawing when an antistatic film is formed on the resist film.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A polymer compound comprising a repeating unit shown by the following general formula (1),

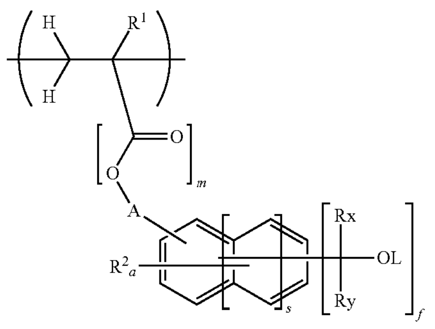

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents 0; "a" represents an integer of 5+2s−f; "m" represents 0 or 1; Rx and Ry represent a hydrogen atom or a substituent shown by the following (i) or (ii), provided that Rx and Ry are not a hydrogen atom at the same time:

(i) a monovalent aromatic group optionally containing a substituent;

(ii) an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx and Ry and directly bonded to the carbon atom bonded to Rx and Ry are not bonded to hydrogen atoms.

2. The polymer compound according to claim 1, further comprising one or more of a repeating unit shown by the following general formula (2) and a repeating unit shown by the following general formula (3), (2)

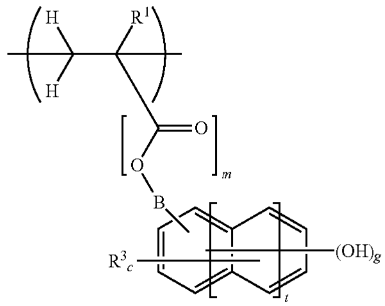

(3)

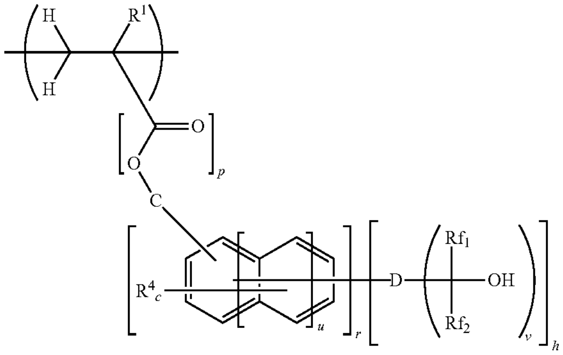

wherein B and C represent a single bond or an alkylene group having 1 to 10 carbon atoms and optionally containing an ether oxygen atom in a chain of the alkylene group; D represent a single bond or a linear, branched, or cyclic v+1-valent aliphatic hydrocarbon group optionally substituted with a fluorine atom and optionally containing an ether oxygen atom, a carbonyl group, or a carbonyloxy group in a chain of the hydrocarbon group; $R^1$ represents a hydrogen atom, a fluorine atom, a methyl group, or a trifluoromethyl group; $R^3$ and $R^4$ independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; $Rf^1$ and $Rf^2$ represent an alkyl group having 1 to 6 carbon atoms and at least one fluorine atom, and $Rf^1$ and D may be bonded to form a ring together with the carbon atom to which $Rf^1$ and Dare bonded; "g" represents an integer of 0 to 3; "h" represents 1 or 2; "r" represents 0 or 1; "v" represents 1 or 2; "t" and "u" represent an integer of 0 to 2; "b" represents an integer of 5+2t−g; "c" represents an integer of 5+2u−h; and "n" and "p" independently represent 0 or 1, provided that when "r" is 0, "p" is 1 and C is a single bond.

3. The polymer compound according to claim 1, further comprising one or more of a repeating unit shown by the following general formula (4) and a repeating unit shown by the following general formula (5), (4)

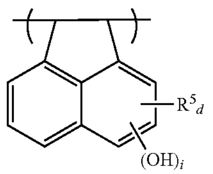

(5)

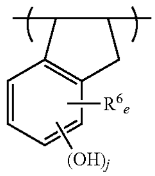

wherein R5 and R6 independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; "i" and "j" represent an integer of 0 to 3; "d" represents an integer of 0 to 5; and "e" represents an integer of 0 to 3.

4. The polymer compound according to claim 2, further comprising one or more of a repeating unit shown by the following general formula (4) and a repeating unit shown by the following general formula (5), (4)

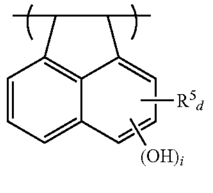

-continued (5)

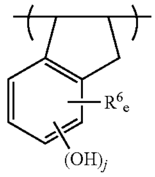

wherein R5 and R6 independently represent a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; "i" and "j" represent an integer of 0 to 3; "d" represents an integer of 0 to 5; and "e" represents an integer of 0 to 3.

5. The polymer compound according to claim 1, further comprising one or more of a repeating unit shown by the following general formula (a1), a repeating unit shown by the following general formula (a2), and a repeating unit shown by the following general formula (a3), (a1)

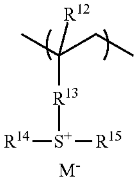

(a2)

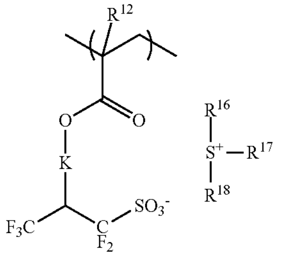

(a3)

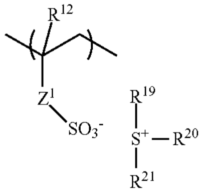

wherein $R^{12}$ independently represents a hydrogen atom or a methyl group; R13 represents a single bond, a phenylene group, —O—$R^{22}$—, or —C(═O)—$Z^2$—$R^{22}$—, where $Z^2$ represents an oxygen atom or NH, and $R^{22}$ represents a phenylene group or a linear, branched, or cyclic alkylene group or alkenylene group having 1 to 6 carbon atoms and optionally containing a carbonyl group, an ester group, an ether group, or a hydroxyl group; K represents a single bond or —$Z^3$—C(═O)—O—, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, -0_$R^{23}$_, or —C(=0)-$Z^4$—$R^{23}$_, where $Z^4$ represents an oxygen atom or NH, and $R^{23}$ represents a phenylene group or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

6. The polymer compound according to claim 2, further comprising one or more of a repeating unit shown by the following general formula (a1), a repeating unit shown by the following general formula (a2), and a repeating unit shown by the following general formula (a3), (a1)

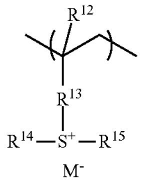

(a2)

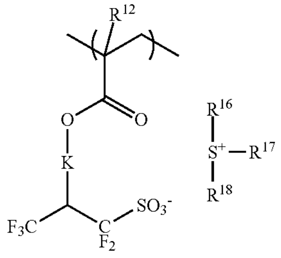

(a3)

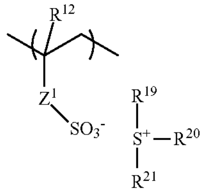

wherein $R^{12}$ independently represents a hydrogen atom or a methyl group; $R^{13}$ represents a single bond, a phenylene group, —O—$R^{22}$—, or —C(═O)—$Z^{22}$_, where $Z^2$ represents an oxygen atom or NH, and $R^{22}$ represents a phenylene group or a linear, branched, or cyclic alkylene group or alkenylene group having 1 to 6 carbon atoms and optionally containing a carbonyl group, an ester group, an ether group, or a hydroxyl group; K represents a single bond or —$Z^3$—C(═O)—O—, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, —O—$R^{23}$—, or —C(═O)—$Z^4$—$R^{23}$—, where $Z^4$ represents an oxygen atom or NH, and R23 represents a phenylene group or a linear, branched, or cyclic alkylene group or alkenylene group having 1 to 6 carbon atoms and optionally containing a carbonyl group, an ester group, an ether group, or a hydroxyl group; M represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

7. The polymer compound according to claim 3, further comprising one or more of a repeating unit shown by the following general formula (a1), a repeating unit shown by the following general formula (a2), and a repeating unit shown by the following general formula (a3), (a1)

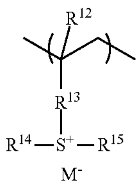

(a2)

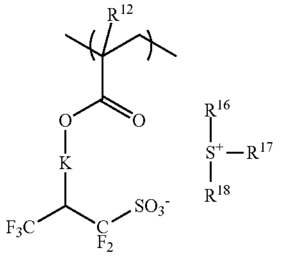

(a3)

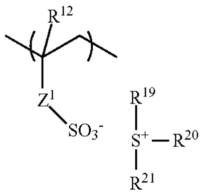

wherein $R^{12}$ independently represents a hydrogen atom or a methyl group; $R^{13}$ represents a single bond, a phenylene group, —O—$R^{22}$—, —C(═O) where $Z^2$ represents an oxygen atom or NH, and $R^{22}$ represents a phenylene group or a linear, branched, or cyclic alkylene group or alkenylene group having 1 to 6 carbon atoms and optionally containing a carbonyl group, an ester group, an ether group, or a hydroxyl group; K represents a single bond or —$Z^3$—C(═O)'—O—, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, —O—$R^{23}$—, or —C(═O)—$Z^4$—$R^{23}$—, where $Z^4$ represents an oxygen atom or NH, and $R^{23}$ represents a phenylene group or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

8. The polymer compound according to claim 4, further comprising one or more of a repeating unit shown by the following general formula (a1), a repeating unit shown by the following general formula (a2), and a repeating unit shown by the following general formula (a3), (a1)

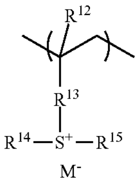

(a2)

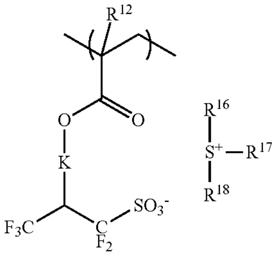

(a3)

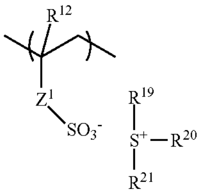

wherein $R^{12}$ independently represents a hydrogen atom or a methyl group; $R^{13}$ represents a single bond, a phenylene group, —O—$R^{22}$—, or —C(═O)—$Z^2$—$R^{22}$—, where $Z^2$ represents an oxygen atom or NH, and R22 represents a phenylene group or a linear, branched, or cyclic alkylene group or alkenylene group having 1 to 6 carbon atoms and optionally containing a carbonyl group, an ester group, an ether group, or a hydroxyl group; K represents a single bond or —$Z^3$—C(═O)—O—, where $Z^3$ represents a linear, branched, or cyclic divalent hydrocarbon group having 1 to 20 carbon atoms and optionally substituted with a heteroatom; $Z^1$ represents a single bond, a methylene group, an ethylene group, a phenylene group, a fluorinated phenylene group, —O—$R^{23}$—, or —C(═O)—$Z^4$—$R^{23}$—, where $Z^4$ represents an oxygen atom or NH, and $R^{23}$ represents a phenylene group or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $R^{14}$, $R^{15}$, $R^{16}$, $R^{17}$, $R^{18}$, $R^{19}$, $R^{20}$, and $R^{21}$ independently represent a linear monovalent hydrocarbon group having 1 to 20 carbon atoms or a branched or cyclic monovalent hydrocarbon group having 3 to 20 carbon atoms, each optionally substituted with or containing a heteroatom, $R^{14}$ and $R^{15}$ may be bonded to each other to form a ring together with the sulfur atom in the formula, and two or more of $R^{16}$, $R^{17}$, and $R^{18}$ or two or more of $R^{19}$, $R^{20}$, and $R^{21}$ may be bonded to each other to form a ring together with the sulfur atom in the formula.

9. A negative resist composition comprising the polymer compound according to claim 1.

10. A negative resist composition comprising the polymer compound according to claim 2.

11. A negative resist composition comprising the polymer compound according to claim 3.

12. A negative resist composition comprising the polymer compound according to claim 4.

13. The negative resist composition according to claim 9, further comprising a compound capable of generating acid by irradiation with a high energy beam.

14. The negative resist composition according to claim 9 or 6, further comprising a salt shown by the following general formula (3a), $$R^{11}CO_2^-Q^+ \quad (3a)$$

wherein RII represents a linear, branched, or cyclic alkyl group having 1 to 20 carbon atoms, alkenyl group having 2 to 20 carbon atoms, aryl group having 6 to 36 carbon atoms, in which these groups optionally contain a fluorine atom, a nitrogen atom, an ether group, an ester group, a lactone ring, a lactam ring, a carbonyl group, or a hydroxyl group; Q represents a counter cation having a substituent selected from a sulfonium cation, an iodonium cation, and an ammonium cation.

15. A laminate comprising a resist film formed from the negative resist composition according to claim 9 on a photomask blank.

16. A patterning process comprising the steps of: forming a resist film from the negative resist composition according to claim 9 on a substrate to be processed; pattern-irradiating the resist film with a high energy beam; and developing the resist film with an alkaline developer to form a resist pattern.

17. The patterning process according to claim 16, wherein the high energy beam is an EUV or an electron beam.

18. The patterning process according to claim 16, wherein the substrate to be processed is a photomask blank.

19. The patterning process according to claim 18, wherein an outermost surface of the photomask blank is formed of a chromium material.

20. A compound shown by the following general formula (1a), (1a)

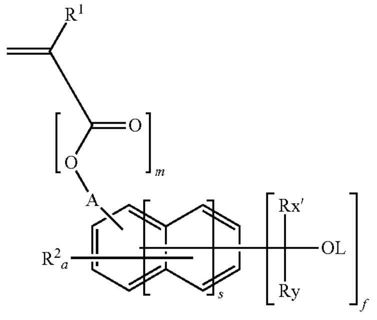

wherein A represents a single bond or an alkylene group having 1 to 10 carbon atoms and optionally containing an ether oxygen atom in a chain of the alkylene group; $R^1$ represents a hydrogen atom, a fluorine atom, a methyl group, or a trifluoromethyl group; $R^2$ represents a hydrogen atom, a halogen atom, a linear, branched, or cyclic acyloxy group having 2 to 8 carbon atoms and optionally substituted with halogen, a linear, branched, or cyclic alkyl group having 1 to 6 carbon atoms and optionally substituted with halogen, or a linear, branched, or cyclic alkoxy group having 1 to 6 carbon atoms and optionally substituted with halogen; L represents a hydrogen atom, a linear, branched, or cyclic monovalent aliphatic hydrocarbon group having 1 to 10 carbon atoms and optionally containing an ether oxygen atom, a carbonyl group, or a carbonyloxy group in a chain of the hydrocarbon group, or a monovalent aromatic group optionally containing a substituent; "f" represents an integer of 1 to 3; "s" represents 0; "a" represents an integer of 5+2s−f; "m" represents 0 or 1; Rx' and Ry' represent a hydrogen atom, or an alkyl group having 1 to 15 carbon atoms or an aralkyl group having 7 to 15 carbon atoms, each optionally substituted with a halogen atom except for fluorine, a hydroxyl group, or an alkoxy group, in which carbon atoms contained in Rx' and Ry' and directly bonded to the carbon atom bonded to Rx' and Ry' are not bonded to hydrogen atoms, and Rx' and Ry' are not a hydrogen atom at the same time.

* * * * *